(12) United States Patent
Komori et al.

(10) Patent No.: US 7,999,136 B2
(45) Date of Patent: *Aug. 16, 2011

(54) AMIDE COMPOUND AND USE THEREOF

(75) Inventors: Takashi Komori, Tokyo (JP); Mayumi Kubota, Toyonaka (JP); Yuichi Matsuzaki, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/451,116

(22) PCT Filed: Apr. 25, 2008

(86) PCT No.: PCT/JP2008/058029
§ 371 (c)(1),
(2), (4) Date: Oct. 27, 2009

(87) PCT Pub. No.: WO2008/136385
PCT Pub. Date: Nov. 13, 2008

(65) Prior Publication Data
US 2010/0056640 A1     Mar. 4, 2010

(30) Foreign Application Priority Data
Apr. 27, 2007 (JP) .................. 2007-118645

(51) Int. Cl.
C07C 233/65 (2006.01)
A01N 37/18 (2006.01)

(52) U.S. Cl. ....................... 564/176; 514/622

(58) Field of Classification Search ............ 564/176; 514/622
See application file for complete search history.

(56) References Cited

U.S. PATENT DOCUMENTS

| 4,946,865 | A | 8/1990 | Takahashi et al. |
| 7,714,168 | B2 * | 5/2010 | Komori .................... 564/176 |
| 2004/0049065 | A1 | 3/2004 | Craig et al. |
| 2004/0248739 | A1 | 12/2004 | Schaetzer et al. |
| 2008/0319080 | A1 | 12/2008 | Komori |
| 2009/0131531 | A1 | 5/2009 | Komori |

FOREIGN PATENT DOCUMENTS

| EP | 1295868 | * | 3/2003 |
| EP | 1 770 085 | A1 | 4/2007 |
| JP | 63-154601 | | 6/1988 |
| JP | 2004-74537 | | 3/2004 |
| WO | 03/104206 | | 12/2003 |
| WO | 2004/002981 | | 1/2004 |
| WO | 2007/049728 | | 5/2007 |
| WO | 2007/049729 | | 5/2007 |
| WO | 2008/136387 | | 11/2008 |
| WO | 2008/136388 | | 11/2008 |
| WO | 2008/136389 | | 11/2008 |
| WO | 2009/004978 | | 1/2009 |
| WO | 2009/011305 | | 1/2009 |

OTHER PUBLICATIONS

Supplementary European Search Report issued Mar. 25, 2010 in European Patent Application No. 08752103.5.
Linda J. Ejim et al., "Inhibitors of Bacterial Cystathionine β-Lyase: Leads for New Antimicrobial Agents and Probes of Enzyme Structure and Function", J. Med. Chem., 50(4), 755-764 (2007).
Jun-Ying Nie et al., "Synthesis of fluoro- and polyfluoro-veratraldehydes by electrophilic fluorination", Journal of Fluorine Chemistry, 74(2), 297-301 (1995).
International Search Report issued Jul. 15, 2008 in International (PCT) Application No. PCT/JP2008/058029.
Abstract of JP 2007-145816, published Jun. 14, 2007.
Abstract of JP 2007-145817, published Jun. 14, 2007.
Abstract of JP 63-027450, published Feb. 5, 1988.

* cited by examiner

*Primary Examiner* — Shailendra Kumar
(74) *Attorney, Agent, or Firm* — Wenderoth, Lind & Ponack, L.L.P.

(57) ABSTRACT

Disclosed is an amide compound represented by the formula (1) below, which has excellent plant disease controlling activity. (1) (In the formula, substituents represented by A, Z, $X^1$, $X^2$ and $X^3$ and the like are as defined in the description.)

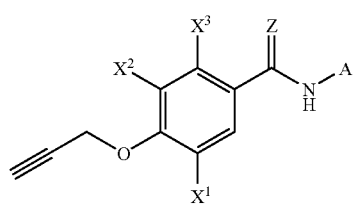

18 Claims, No Drawings

AMIDE COMPOUND AND USE THEREOF

This application is a 371 of PCT/JP2008/058029, filed Apr. 25, 2008.

TECHNICAL FIELD

The present invention relates to an amide compound and use thereof.

BACKGROUND ART

Heretofore, chemicals for controlling plant diseases have been developed, and compounds having plant disease control activity have been found and are now served for practical use.

DISCLOSURE OF THE INVENTION

Problem to be Solved by the Invention

An object of the present invention is to provide a compound having excellent plant disease control activity.

Means for Solving the Problem

The present inventors have intensively studied so as to find a compound having excellent plant disease control activity. As a result, they have found that an amide compound represented by the following formula (1) has excellent plant disease control activity, and thus the present invention has been completed.

That is, the present invention provides an amide compound represented by the formula (1):

[Chemical Formula 1]

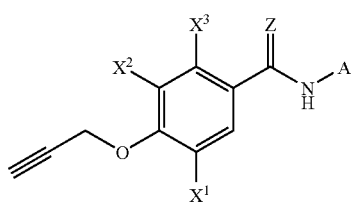

(1)

wherein $X^1$ represents a fluorine atom or a methoxy group; $X^2$ represents a hydrogen atom, a halogen atom, a C1-C4 alkyl group, a C2-C4 alkenyl group, a C2-C4 alkynyl group, a C1-C4 haloalkyl group, a C1-C4 alkoxy group, a C1-C4 alkylthio group, a hydroxy C1-C4 alkyl group, a nitro group, a cyano group, a formyl group, an $NR^1R^2$ group, a $CO_2R^3$ group, a $CONR^4R^5$ group, or a phenyl group optionally substituted with at least one group selected from the group consisting of a methyl group, a halogen atom, a cyano group and a nitro group; $X^3$ represents a halogen atom, a C1-C4 alkyl group, a C2-C4 alkenyl group, a C2-C4 alkynyl group, a C1-C4 haloalkyl group, a C1-C4 alkoxy group, a C1-C4 alkylthio group, a nitro group, a cyano group, a formyl group, an $NR^6R^7$ group, a $CO_2R^8$ group, a $CONR^9R^{10}$ group, or a phenyl group optionally substituted with at least one group selected from the group consisting of a methyl group, a halogen atom, a cyano group and a nitro group; Z represents an oxygen atom or a sulfur atom; A represents $A^1$-$CR^{11}R^{12}R^{13}$ or $A^2$-Cy; $A^1$ represents a single bond or a $CH_2$ group; $A^2$ represents a single bond, a $CH_2$ group, a $CH(CH_3)$ group, a $C(CH_3)_2$ group or a $CH(CH_2CH_3)$ group; Cy represents a C3-C6 cycloalkyl group optionally substituted with at least one group selected from the group consisting of a C1-C4 alkyl group, a C2-C4 alkenyl group, a C2-C4 alkynyl group, a halogen atom, a hydroxyl group, a cyano group, a carboxyl group and a C2-C5 alkoxycarbonyl group; $R^1$ and $R^2$ independently represent a hydrogen atom, a C1-C4 alkyl group, a C3-C4 alkenyl group, a C3-C4 alkynyl group, a C2-C4 haloalkyl group, a C2-C5 alkylcarbonyl group, a C2-C5 alkoxycarbonyl group or a C1-C4 alkylsulfonyl group; $R^3$ represents a C1-C4 alkyl group, a C3-C4 alkenyl group or a C3-C4 alkynyl group; $R^4$ represents a hydrogen atom, a C1-C4 alkyl group, a C3-C4 alkenyl group, a C3-C4 alkynyl group, a C2-C4 haloalkyl group, a C2-C5 alkylcarbonyl group, a C2-C5 alkoxycarbonyl group or a C1-C4 alkylsulfonyl group; $R^5$ represents a hydrogen atom, a C1-C4 alkyl group, a C3-C4 alkenyl group, a C3-C4 alkynyl group or a C2-C4 haloalkyl group; $R^6$ and $R^7$ independently represent a hydrogen atom, a C1-C4 alkyl group, a C3-C4 alkenyl group, a C3-C4 alkynyl group, a C2-C4 haloalkyl group, a C2-C5 alkylcarbonyl group, a C2-C5 alkoxycarbonyl group or a C1-C4 alkylsulfonyl group; $R^8$ represents a C1-C4 alkyl group, a C3-C4 alkenyl group or a C3-C4 alkynyl group; $R^9$ represents a hydrogen atom, a C1-C4 alkyl group, a C3-C4 alkenyl group, a C3-C4 alkynyl group, a C2-C4 haloalkyl group, a C2-C5 alkylcarbonyl group, a C2-C5 alkoxycarbonyl group or a C1-C4 alkylsulfonyl group; $R^{10}$ represents a hydrogen atom, a C1-C4 alkyl group, a C3-C4 alkenyl group, a C3-C4 alkynyl group or a C2-C4 haloalkyl group; $R^{11}$ and $R^{12}$ independently represent a C1-C4 alkyl group; and $R^{13}$ represents a hydrogen atom, a C1-C4 alkyl group, a C2-C4 alkenyl group, a C2-C4 alkynyl group, a cyano group, a carboxyl group or a C2-C5 alkoxycarbonyl group (hereinafter referred to as the present compound); a plant disease control agent comprising the present compound as an active ingredient; and a method for controlling a plant disease, which comprises treating a plant or soil with an effective amount of the present compound.

EFFECTS OF THE INVENTION

The present compound is useful as an active ingredient for a plant disease control agent because of its excellent plant disease control activity.

BEST MODE FOR CARRYING OUT THE INVENTION

In the present invention, examples of the halogen atom represented by $X^2$ include a fluorine atom, a chlorine atom, a bromine atom and an iodine atom;

Examples of the C1-C4 alkyl group include a methyl group, an ethyl group, a 1-methylethyl group, a 1,1-dimethylethyl group, a propyl group and a 1-methylpropyl group;

Examples of the C2-C4 alkenyl group include a vinyl group, a 1-propenyl group, a 2-propenyl group, a 2-butenyl group and a 3-butenyl group;

Examples of the C2-C4 alkynyl group include an ethynyl group, a 1-propynyl group, a 2-propynyl group and a 3-butynyl group;.

Examples of the C1-C4 haloalkyl group include a fluoromethyl group, a chloromethyl group, a bromomethyl group, a difluoromethyl group, a dichloromethyl group, a dibromomethyl group, a trifluoromethyl group, a trichloromethyl group, a dichlorofluoromethyl group, a chlorodifluoromethyl group, a 1,1-difluoroethyl group, a 2,2,2- trifluoroethyl group, a 2-fluoroethyl group, a 3-fluoropropyl group, a 4-fluorobutyl group and a 1-chloroethyl group;

Examples of the C1-C4 alkoxy group include a methoxy group, an ethoxy group, a 1-methylethoxy group, a 1,1-dimethylethoxy group, a propoxy group, a 1-methylpropoxy group, a 2-methylpropoxy group and a butoxy group;

Examples of the C1-C4 alkylthio group include a methylthio group, an ethylthio group, a 1-methylethylthio group, a 1,1-dimethylethylthio group, a propylthio group and a 1-methylpropylthio group;

Examples of the hydroxy C1-C4 alkyl group include a hydroxymethyl group, a 1-hydroxyethyl group and a 2-hydroxyethyl group;

Examples of the phenyl group optionally substituted with at least one group selected from the group consisting of a methyl group, a halogen atom, cyano group and a nitro group include a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a 4-cyanophenyl group and a 4-nitrophenyl group;

Examples of the halogen atom represented by $X^3$ include a fluorine atom, a chlorine atom, a bromine atom and an iodine atom;

Examples of the C1-C4 alkyl group include a methyl group, an ethyl group, a 1-methylethyl group, a 1,1-dimethylethyl. group, a propyl group and a 1-methylpropyl group;

Examples of the C2-C4 alkenyl group include a vinyl group, a 1-propenyl group, a 2-propenyl group, a 2-butenyl group and a 3-butenyl group;

Examples of the C2-C4 alkynyl group include an ethynyl group, a 1-propynyl group, a 2-propynyl group and a 3-butynyl group;

Examples of the C1-C4 haloalkyl group include a fluoromethyl group, a chloromethyl group, a bromomethyl group, a difluoromethyl group, a dichloromethyl group, a dibromomethyl group, a trifluoromethyl group, a trichloromethyl group, a dichlorofluoromethyl group, a chlorodifluoromethyl group, a 1,1-difluoroethyl group, a 2,2,2-trifluoroethyl group, a 2-fluoroethyl group, a 3-fluoropropyl group, a 4-fluorobutyl group and a 1-chloroethyl group;

Examples of the C1-C4 alkoxy group include a methoxy group, an ethoxy group, a 1-methylethoxy group, a 1,1-dimethylethoxy group, a propoxy group, a 1-methylpropoxy group, a 2-methylpropoxy group and a butoxy group;

Examples of the C1-C4 alkylthio group include a methylthio group, an ethylthio group, a 1-methylethylthio group, a 1,1-dimethylethylthio group, a propylthio group and a 1-methylpropylthio group;

Examples of the phenyl group optionally substituted with at least one group selected from the group consisting of a methyl group, a halogen atom, a cyano group and a nitro group include a phenyl group, a 2-methylphenyl group, a 3-methylphenyl group, a 4-methylphenyl group, a 2-fluorophenyl group, a 3-fluorophenyl group, a 4-fluorophenyl group, a 2-chlorophenyl group, a 3-chlorophenyl group, a 4-chlorophenyl group, a 4-cyanophenyl group and a 4-nitrophenyl group;

Examples of the C1-C4 alkyl group represented by $R^1$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C2-C4 haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group;

Examples of the C2-C5 alkylcarbonyl group include an acetyl group, an ethylcarbonyl group, a 1-methylethylcarbonyl group and a 1,1-dimethylethylcarbonyl group;

Examples of the C2-C5 alkoxycarbonyl group include a methoxycarbonyl group, an ethoxycarbonyl group, a 1-methylethoxycarbonyl group and a 1,1-dimethylethoxycarbonyl group;

Examples of the C1-C4 alkylsulfonyl group include a methylsulfonyl group, an ethylsulfonyl group, a 1-methylethylsulfonyl group and a 1,1-dimethylethylsulfonyl group;

Examples of the C1-C4 alkyl group represented by $R^2$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C2-C4 haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group;

Examples of the C2-C5 alkylcarbonyl group include an acetyl group, an ethylcarbonyl group, a 1-methylethylcarbonyl group and a 1,1-dimethylethylcarbonyl group;

Examples of the C2-C5 alkoxycarbonyl group include a methoxycarbonyl group, an ethoxycarbonyl group, a 1-methylethoxycarbonyl group and a 1,1-dimethylethoxycarbonyl group;

Examples of the C1-C4 alkylsulfonyl group include a methylsulfonyl group, an ethylsulfonyl group, a 1-methylethylsulfonyl group and a 1,1-dimethylethylsulfonyl group;

Examples of the C1-C4 alkyl group represented by $R^3$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include an ethynyl group, a 1-propynyl group, a 2-propynyl group and a 3-butynyl group;

Examples of the C1-C4 alkyl group represented by $R^4$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C2-C4 haloalkyl group include a 1,1-difluoroethyl group, a 2,2,2-trifluoroethyl group, a 2-fluoroethyl group, a 3-fluoropropyl group, a 4-fluorobutyl. group and a 1-chloroethyl group;

Examples of the C2-C5 alkylcarbonyl group include an acetyl group, an ethylcarbonyl group, a 1-methylethylcarbonyl group and a 1,1-dimethylethylcarbonyl group;

Examples of the C2-C5 alkoxycarbonyl group include a methoxycarbonyl group, an ethoxycarbonyl group, a 1-methylethoxycarbonyl group and a 1,1-dimethylethoxycarbonyl group;

Examples of the C1-C4 alkylsulfonyl group include a methylsulfonyl group, an ethylsulfonyl group, a 1-methylethylsulfonyl group and a 1,1-dimethylethylsulfonyl group;

Examples of the C1-C4 alkyl group represented by $R^5$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C2-C4 haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group;

Examples of the $NR^1R^2$ group include an amino group, a methylamino group, a dimethylamino group, an ethylamino group, a 2-propenylamino group, a 2-propynylamino group, a 2-chloroethylamino group, an acetylamino group, a propionylamio group, a 1,1-dimethylethylcarbonylamino group, a methoxycarbonylamino group, an ethoxycarbonylamino group, a methanesulfonylamino group, an N-acetyl-N-methylamino group, an N-ethoxycarbonyl-N-methylamino group and an N-methanesulfonyl-N-methylamino group;

Examples of the $CONR^4R^5$ group include a carbamoyl group, a methylcarbamoyl group, a dimethylcarbamoyl group, an ethylmethylcarbamoyl group, a (2-propenyl)carbamoyl group, a (2-propynyl)carbamoyl group and a 2-chloroethylcarbamoyl group;

Examples of the C1-C4 alkyl group represented by $R^6$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C2-C4 haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group;

Examples of the C2-C5 alkylcarbonyl group include an acetyl group, an ethylcarbonyl group, a 1-methylethylcarbonyl group and a 1,1-dimethylethylcarbonyl group;

Examples of the C2-C5 alkoxycarbonyl group include a methoxycarbonyl group, an ethoxycarbonyl group, a 1-methylethoxycarbonyl group and a 1,1-dimethylethoxycarbonyl group;

Examples of the C1-C4 alkylsulfonyl group include a methylsulfonyl group, an ethylsulfonyl group, a 1-methylethylsulfonyl group and a 1,1-dimethylethylsulfonyl group;

Examples of the C1-C4 alkyl group represented by $R^7$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C2-C4 haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group;

Examples of the C2-C5 alkylcarbonyl group include an acetyl group, an ethylcarbonyl group, a 1-methylethylcarbonyl group and a 1,1-dimethylethylcarbonyl group;

Examples of the C2-C5 alkoxycarbonyl group include a methoxycarbonyl group, an ethoxycarbonyl group, a 1-methylethoxycarbonyl group and a 1,1-dimethylethoxycarbonyl group;

Examples of the C1-C4 alkylsulfonyl group include a methylsulfonyl group, an ethylsulfonyl group, a 1-methylethylsulfonyl group and a 1,1-dimethylethylsulfonyl group;

Examples of the C1-C4 alkyl group represented by $R^8$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C1-C4 alkyl group represented by $R^9$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C2-C4 haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group;

Examples of the C2-C5 alkylcarbonyl group include an acetyl group, an ethylcarbonyl group, a 1-methylethylcarbonyl group and a 1,1-dimethylethylcarbonyl group;

Examples of the C2-C5 alkoxycarbonyl group include a methoxycarbonyl group, an ethoxycarbonyl group, a 1-methylethoxycarbonyl group and a 1,1-dimethylethoxycarbonyl group;

Examples of the C1-C4 alkylsulfonyl group include a methylsulfonyl group, an ethylsulfonyl group, a 1-methylethylsulfonyl group and a 1,1-dimethylethylsulfonyl group;

Examples of the C1-C4 alkyl group represented by $R^{10}$ include a methyl group, an ethyl group, a 1-methylethyl group, a 1,1-dimethylethyl group, a propyl group and a 1-methylpropyl group;

Examples of the C3-C4 alkenyl group include a 1-propenyl group, a 2-propenyl group, a 2-butenyl group and a 3-butenyl group;

Examples of the C3-C4 alkynyl group include a 1-propynyl group, a 2-propynyl group and a 3-butynyl group;

Examples of the C2-C4 haloalkyl group include a 1,1-difluoroethyl group, a 2,2,2-trifluoroethyl group, a 2-fluoroethyl group, a 3-fluoropropyl group, a 4-fluorobutyl group and a 1-chloroethyl group;

Examples of the $NR^6R^7$ group include an amino group, a methylamino group, a dimethylamino group, an ethylamino group, a 2-propenylamino group, a 2-propynylamino group, a 2-chloroethylamino group, an acetylamino group, a propionylamio group, a 1,1-dimethylethylcarbonylamino group, an N-methoxycarbonylamino group, an ethoxycarbonylamino group, a methanesulfonylamino group, an acetyl-N-methylamino group, an N-ethoxycarbonyl-N-methylamino group and an N-methanesulfonyl-N-methylamino group;

Examples of the $CONR^9R^{10}$ group include a carbamoyl group, a methylcarbamoyl group, a dimethylcarbamoyl group, an ethylmethylcarbamoyl group, a (2-propenyl)carbamoyl group, a (2-propynyl)carbamoyl group and a 2-chloroethylcarbamoyl group;

Examples of the C1-C4 alkyl group represented by $R^{11}$ include a methyl group, an ethyl group, a 1-methylethyl group, a 1,1-dimethylethyl group, a propyl group and a 1-methylpropyl group;

Examples of the C1-C4 alkyl group represented by $R^{12}$ include a methyl group, an ethyl group, a 1-methylethyl group, a 1,1-dimethylethyl group, a propyl group and a 1-methylpropyl group;

Examples of the C1-C4 alkyl group represented by $R^{13}$ include a methyl group, an ethyl group, a 1-methylethyl group, a 1,1-dimethylethyl group, a propyl group and a 1-methylpropyl group;

Examples of the C2-C4 alkenyl group include a vinyl group, a 1-propenyl group, a 2-propenyl group, a 2-butenyl group and a 3-butenyl group;

Examples of the C2-C4 alkynyl group include an ethynyl group, a 1-propynyl group, a 2-propynyl group and a 3-butynyl group; and Examples of the C2-C5 alkoxycarbonyl group include a methoxycarbonyl group, an ethoxycarbonyl group and a 1-methylethoxycarbonyl group.

In a C3-C6 cycloalkyl group represented by Cy, which is optionally substituted with at least one -substituent selected from the group consisting of a C1-C4 alkyl group, a C2-C4 alkenyl group, a C2-C4 alkynyl group, a halogen atom, a hydroxyl group, a cyano group, a carboxyl group and a C2-C5 alkoxycarbonyl group, examples of the C1-C4 alkyl group as the substituent include a methyl group, an ethyl group, a propyl group and an isopropyl group;

examples of the C2-C4 alkenyl group include a vinyl group, a 1-propenyl group, a 2-propenyl group, a 2-butenyl group and a 3-butenyl group;

examples of the C2-C4 alkynyl group include an ethynyl group, a 1-propynyl group, a 2-propynyl group and a 3-butynyl group;

examples of the halogen atom include a fluorine atom, a chlorine atom, a bromine atom and an iodine atom;

examples of the C2-C5 alkoxycarbonyl group include a methoxycarbonyl group and an ethoxycarbonyl group; and in the C3-C6 cycloalkyl group represented by Cy, which is optionally substituted with at least one substituent selected from the group consisting of a C1-C4 alkyl group, a C2-C4 alkenyl group, a C2-C4 alkynyl group, a halogen atom, a hydroxyl group, a cyano group, a carboxyl group and C2-C5 an alkoxycarbonyl group, examples of the C3-C6 cycloalkyl group include a cyclopropyl group, a cyclobutyl group, a cyclopentyl group and a cyclohexyl group.

As the group represented by $A^2$-Cy, specifically, there are, for example, following groups:

a cyclopropyl group, a 2,2,3,3-tetramethylcyclopropyl group; a cyclobutyl group;

a cyclopentyl group, a 2-methylcyclopentyl group, a 2-hydroxycyclopentyl group, a 2-chlorocyclopentyl group, a 2-bromocyclopentyl group, a 2,2-dimethylcyclopentyl group, a 2-fluoro-2-methylcyclopentyl group, a 2-chloro-2-methylcyclopentyl group, a 2-hydroxy-2-methylcyclopentyl group, a 2,2-difluorocyclopentyl group and a 3-methylcyclopentyl group;

a cyclohexyl group, a 1-methylcyclohexyl group, a 2-methylcyclohexyl group, a 3-methylcyclohexyl group, a 4-methylcyclohexyl group, a 2-trifluoromethylcyclohexyl group, a 2,2-dimethylcyclohexyl group, a 2-fluoro-2-methylcyclohexyl group, a 2-chloro-2-methylcyclohexyl group, a 2-hydroxy-2-methylcyclohexyl group, a 2,2-difluorocyclohexyl group, a 2,3-dimethylcyclohexyl group, a 2,6-dimethylcyclohexyl group, a 2-ethylcyclohexyl group, a 2-chlorocyclohexyl group, a 2-fluorocyclohexyl group, a 2-bromocyclohexyl group, a 2-iodocyclohexyl group, a 2-hydroxycyclohexyl group, a 1-cyanocyclohexyl group, a 2-cyanocyclohexyl group, a 1-carboxycyclohexyl group, a 1-(methoxycarbonyl)cyclohexyl group, a 1-(ethoxycarbonyl)cyclohexyl group, a 2-(methoxycarbonyl)cyclohexyl group and a 2-(ethoxycarbonyl)cyclohexyl group;

a cyclopropylmethyl group, a (1-methylcyclopropyl)methyl group, a (2-methylcyclopropyl)methyl group, a (1-hydroxycyclopropyl)methyl group, a (2-hydroxycyclopropyl)methyl group, a (2,2,3,3-tetramethylcyclopropyl)methyl group, a (1-fluorocyclopropyl)methyl group, a (1-chlorocyclopropyl)methyl group, a (1-cyanocyclopropyl)methyl group, a (1-ethoxycarbonylcyclopropyl)methyl group and a (1-methoxycarbonylcyclopropyl)methyl group;

a cyclobutylmethyl group, a (1-methylcyclobutyl)methyl group, a (2-methylcyclobutyl)methyl group, a (3-methylcyclobutyl)methyl group, a (1-hydroxycyclobutyl)methyl group, a (2-hydroxycyclobutyl)methyl group, a (3-hydroxycyclobutyl)methyl group, a (1-fluorocyclobutyl)methyl group, a (1-chlorocyclobutyl)methyl group, a (1-cyanocyclobutyl)methyl group, a (1-ethoxycarbonylcyclobutyl)methyl group and a (1-methoxycarbonylcyclobutyl)methyl group;

a cyclopentylmethyl group, a (1-methylcyclopentyl)methyl group, a (2-methylcyclopentyl)methyl group, a (3-methylcyclopentyl)methyl group, a (1-hydroxycyclopentyl)methyl group, a (2-hydroxycyclopentyl)methyl group, a (3-hydroxycyclopentyl)methyl group, a (1-fluorocyclopentyl)methyl group, a (1-chlorocyclopentyl)methyl group, a (1-cyanocyclopentyl)methyl group, a (1-ethoxycarbonylcyclopentyl)methyl group and a (1-methoxycarbonylcyclopentyl)methyl group;

a cyclohexylmethyl group, a (1-methylcyclohexyl)methyl group, a (2-methylcyclohexyl)methyl group, a (3-methylcyclohexyl)methyl group, a (4-methylcyclohexyl)methyl group, a (2,3-dimethylcyclohexyl)methyl group, a (1-hydroxycyclohexyl)methyl group, a (2-hydroxycyclohexyl)methyl group, a (3-hydroxycyclohexyl)methyl group, a (4-hydroxycyclohexyl)methyl group, a (1-fluorocyclohexyl)methyl group, a (1-chlorocyclohexyl)methyl group, (1-cyanocyclohexyl)methyl group, a (1-ethoxycarbonylcyclohexyl)methyl group, a (1-methoxycarbonylcyclohexyl)methyl group, a (1-ethynylcyclohexyl)methyl group, a (2-fluorocyclohexyl)methyl group, a (2-chlorocyclohexyl)methyl group, a (2-cyanocyclohexyl)methyl group, a (2-ethoxycarbonylcyclohexyl)methyl group and a (2-methoxycarbonylcyclohexyl)methyl group;

a 1-(cyclopropyl)ethyl group, a 1-(1-methylcyclopropyl)ethyl group, a 1-(2-methylcyclopropyl)ethyl group, a 1-(1-hydroxycyclopropyl)ethyl group, a 1-(2-hydroxycyclopropyl)ethyl group, a 1-(2,2,3,3-tetramethylcyclopropyl)ethyl group, a 1-(1-fluorocyclopropyl)ethyl group, a 1-(1-chlorocyclopropyl)ethyl group, a 1-(1-cyanocyclopropyl)

ethyl group, a 1-(1-ethoxycarbonylcyclopropyl)ethyl group and a 1-(1-methoxycarbonylcyclopropyl)ethyl group;

a 1-(cyclobutyl)ethyl group, a 1-(1-methylcyclobutyl)ethyl group, a 1-(2-methylcyclobutyl)ethyl group, a 1-(3-methylcyclobutyl)ethyl group, a 1-(1-hydroxycyclobutyl)ethyl group, a 1-(2-hydroxycyclobutyl)ethyl group, a 1-(3-hydroxycyclobutyl)ethyl group, a 1-(1-fluorocyclobutyl)ethyl group, a 1-(1-chlorocyclobutyl)ethyl group, a 1-(1-cyanocyclobutyl)ethyl group, a 1-(1-ethoxycarbonylcyclobutyl)ethyl group and a 1-(1-methoxycarbonylcyclobutyl)ethyl group;

a 1-(cyclopentyl)ethyl group, a 1-(1-methylcyclopentyl)ethyl group, a 1-(2-methylcyclopentyl)ethyl group, a 1-(3-methylcyclopentyl)ethyl group, a 1-(1-hydroxycyclopentyl)ethyl group, a 1-(2-hydroxycyclopentyl)ethyl group, a 1-(3-hydroxycyclopentyl)ethyl group, a 1-(1-fluorocyclopentyl)ethyl group, a 1-(1-chlorocyclopentyl)ethyl group, a 1-(1-cyanocyclopentyl)ethyl group, a 1-(1-ethoxycarbonylcyclopentyl)ethyl group and a 1-(1-methoxycarbonylcyclopentyl)ethyl group;

a 1-(cyclohexyl)ethyl group, a 1-(1-methylcyclohexyl)ethyl group, a 1-(2-methylcyclohexyl)ethyl group, a 1-(3-methylcyclohexyl)ethyl group, a 1-(4-methylcyclohexyl)ethyl group, a 1-(2,3-dimethylcyclohexyl)ethyl group, a 1-(1-hydroxycyclohexyl)ethyl group, a 1-(2-hydroxycyclohexyl)ethyl group, a 1-(3-hydroxycyclohexyl)ethyl group, a 1-(4-hydroxycyclohexyl)ethyl group, a 1-(1-fluorocyclohexyl)ethyl group, a 1-(1-chlorocyclohexyl)ethyl group, a 1-(1-cyanocyclohexyl)ethyl group, a 1-(1-ethoxycarbonylcyclohexyl)ethyl group, a 1-(1-methoxycarbonylcyclohexyl)ethyl group, a 1-(1-ethynylcyclohexyl)ethyl group, a 1-(2-fluorocyclohexyl)ethyl group, a 1-(2-chlorocyclohexyl)ethyl group, a 1-(2-cyanocyclohexyl)ethyl group, a 1-(2-ethoxycarbonylcyclohexyl)ethyl group and a 1-(2-methoxycarbonylcyclohexyl)ethyl group; and a 1-methyl-1-cyclopropylethyl group, a 1-methyl-1-cyclobutylethyl group, a 1-methyl-1-(1-hydroxycyclobutyl)ethyl group, a 1-methyl-1-(1-fluorocyclobutyl)ethyl group, a 1-methyl-1-cyclopentylethyl group, a 1-methyl-1-(1-hydroxycyclopentyl)ethyl group, a 1-methyl-1-(1-fluorocyclopentyl)ethyl group, a 1-methyl-1-cyclohexylethyl group, a 1-methyl-1-(1-hydroxycyclohexyl)ethyl group and a 1-methyl-1-(1-fluorocyclohexyl)ethyl group.

Examples of the present compound include the following aspects:

The amide compound represented by the formula (1), wherein Z is an oxygen atom, $X^1$ is a fluorine atom, and $X^2$ is a hydrogen atom;

The amide compound represented by the formula (1), wherein Z is an oxygen atom, $X^1$ is a fluorine atom, and $X^2$ is a fluorine atom;

The amide compound represented by the formula (1), wherein Z is an oxygen atom, $X^1$ is a fluorine atom, and $X^2$ is a chlorine atom;

The amide compound represented by the formula (1), wherein Z is an oxygen atom, $X^1$ is a fluorine atom, and $X^2$ is a bromine atom;

The amide compound represented by the formula (1), wherein Z is an oxygen atom, $X^1$ is a fluorine atom, and $X^2$ is an iodine atom;

The amide compound represented by the formula (1), wherein Z is an oxygen atom, $X^1$ is a fluorine atom, and $X^2$ is a C1-C4 alkyl group;

The amide compound represented by the formula (1), wherein Z is an oxygen atom, $X^1$ is a fluorine atom, and $X^2$ is a C2-C4 alkenyl group;

The amide compound represented by the formula (1), wherein Z is an oxygen atom, $X^1$ is a fluorine atom, and $X^2$ is a C2-C4 alkynyl group;

The amide compound represented by the formula (1), wherein Z is an oxygen atom, $X^1$ is a fluorine atom, and $X^2$ is a C1-C4 haloalkyl group;

The amide compound represented by the formula (1), wherein Z is an oxygen atom, $X^1$ is a fluorine atom, and $X^2$ is a C1-C4 alkoxy group;

The amide compound represented by the formula (1), wherein Z is an oxygen atom, $X^1$ is a fluorine atom, and $X^2$ is a C1-C4 alkylthio group;

The amide compound represented by the formula (1), wherein Z is an oxygen atom, $X^1$ is a fluorine atom, and $X^2$ is a hydroxy C1-C4 alkyl group;

The amide compound represented by the formula (1), wherein Z is an oxygen atom, $X^1$ is a fluorine atom, and $X^2$ is a nitro group;

The amide compound represented by the formula (1), wherein Z is an oxygen atom, $X^1$ is a fluorine atom, and $X^2$ is a cyano group;

The amide compound represented by the formula (1), wherein Z is an oxygen atom, $X^1$ is a fluorine atom, and $X^2$ is a formyl group;

The amide compound represented by the formula (1), wherein Z is an oxygen atom, $X^1$ is a fluorine atom, and $X^2$ is an $NR^1R^2$ group;

The amide compound represented by the formula (1), wherein Z is an oxygen atom, $X^1$ is a fluorine atom, and $X^2$ is a $CO_2R^3$ group;

The amide compound represented by the formula (1), wherein Z is an oxygen atom, $X^1$ is a fluorine atom, and $X^2$ is a $CONR^4R^5$ group;

The amide compound represented by the formula (1), wherein Z is an oxygen atom, $X^1$ is a fluorine atom, and $X^2$ is a phenyl group optionally substituted with at least one group selected from the group consisting of a methyl group, a halogen atom, a cyano group and a nitro group;

The amide compound represented by the formula (1), wherein Z is an oxygen atom, $X^1$ is a methoxy. group, and $X^2$ is a hydrogen atom;

The amide compound represented by the formula (1), wherein Z is an oxygen atom, $X^1$ is a methoxy group, and $X^2$ is a fluorine atom;

The amide compound represented by the formula (1), wherein Z is an oxygen atom, $X^1$ is a methoxy group, and $X^2$ is a chlorine atom;

The amide compound represented by the formula (1), wherein Z is an oxygen atom, $X^1$ is a methoxy group, and $X^2$ is a bromine atom;

The amide compound represented by the formula (1), wherein Z is an oxygen atom, $X^1$ is a methoxy group, and $X^2$ is an iodine atom;

The amide compound represented by the formula (1), wherein Z is an oxygen atom, $X^1$ is a methoxy group, and $X^2$ is a C1-C4 alkyl group;

The amide compound represented by the formula (1), wherein Z is an oxygen atom, $X^1$ is a methoxy group, and $X^2$ is a C2-C4 alkenyl group;

The amide compound represented by the formula (1), wherein Z is an oxygen atom, $X^1$ is a methoxy group, and $X^2$ is a C2-C4 alkynyl group;

The amide compound represented by the formula (1), wherein Z is an oxygen atom, $X^1$ is a methoxy group, and $X^2$ is a C1-C4 haloalkyl group;

The amide compound represented by the formula (1), wherein Z is an oxygen atom, $X^1$ is a methoxy group, and $X^2$ is a C1-C4 alkoxy group;

The amide compound represented by the formula (1), wherein Z is an oxygen atom, $X^1$ is a methoxy group, and $X^2$ is a C1-C4 alkylthio group;

The amide compound represented by the formula (1), wherein Z is an oxygen atom, $X^1$ is a methoxy group, and $X^2$ is a hydroxy C1-C4 alkyl group;

The amide compound represented by the formula (1), wherein Z is an oxygen atom, $X^1$ is a methoxy group, and $X^2$ is a nitro group;

The amide compound represented by the formula (1), wherein Z is an oxygen atom, X is a methoxy group, and $X^2$ is a cyano group;

The amide compound represented by the formula (1), wherein Z is an oxygen atom, $X^1$ is a methoxy group, and $X^2$ is a formyl group;

The amide compound represented by the formula (1), wherein Z is an oxygen atom, $X^1$ is a methoxy group, and $X^2$ is an $NR^1R^2$ group;

The amide compound represented by the formula (1), wherein Z is an oxygen atom, $X^1$ is a methoxy group, and $X^2$ is a $CO_2R^3$ group;

The amide compound represented by the formula (1), wherein Z is an oxygen atom, $X^1$ is a methoxy group, and $X^2$ is a $CONR^4R^5$ group;

The amide compound represented by the formula (1), wherein Z is an oxygen atom, $X^1$ is a methoxy group, and $X^2$ is a phenyl group optionally substituted with at least one group selected from the group consisting of a methyl group, a halogen atom, a cyano group and a nitro group;

The amide compound represented by the formula (1), wherein Z is an oxygen atom, $X^1$ is a fluorine atom, and $X^3$ is a fluorine atom;

The amide compound represented by the formula (1), wherein Z is an oxygen atom, $X^1$ is a fluorine atom, and $X^3$ is a chlorine atom;

The amide compound represented by the formula (1), wherein Z is an oxygen atom, $X^1$ is a fluorine atom, and $X^3$ is a bromine atom;

The amide compound represented by the formula (1), wherein Z is an oxygen atom, $X^1$ is a fluorine atom, and $X^3$ is an iodine atom;

The amide compound represented by the formula (1), wherein Z is an oxygen atom, $X^1$ is a fluorine atom, and $X^3$ is a C1-C4 alkyl group;

The amide compound represented by the formula (1), wherein Z is an oxygen atom, $X^1$ is a fluorine atom, and $X^3$ is a C2-C4 alkenyl group;

The amide compound represented by the formula (1), wherein Z is an oxygen atom, $X^1$ is a fluorine atom, and $X^3$ is a C2-C4 alkynyl group;

The amide compound represented by the formula (1), wherein Z is an oxygen atom, $X^1$ is a fluorine atom, and $X^3$ is a C1-C4 haloalkyl group;

The amide compound represented by the formula (1), wherein Z is an oxygen atom, $X^1$ is a fluorine atom, and $X^3$ is a C1-C4 alkoxy group;

The amide compound represented by the formula (1), wherein Z is an oxygen atom, $X^1$ is a fluorine atom, and $X^3$ is a C1-C4 alkylthio group;

The amide compound represented by the formula (1), wherein Z is an oxygen atom, $X^1$ is a fluorine atom, and $X^3$ is a nitro group;

The amide compound represented by the formula (1), wherein Z is an oxygen atom, $X^1$ is a fluorine atom, and $X^3$ is a cyano group;

The amide compound represented by the formula (1), wherein Z is an oxygen atom, $X^1$ is a fluorine atom, and $X^3$ is a formyl group;

The amide compound represented by the formula (1), wherein Z is an oxygen atom, $X^1$ is a fluorine atom, and $X^3$ is an $NR^6R^7$ group;

The amide compound represented by the formula (1), wherein Z is an oxygen atom, $X^1$ is a fluorine atom, and $X^3$ is a $CO_2R^8$ group;

The amide compound represented by the formula (1), wherein Z is an oxygen atom, $X^1$ is a fluorine atom, and $X^3$ is a $CONR^9R^{10}$ group;.

The amide compound represented by the formula (1), wherein Z is an oxygen atom, $X^1$ is a fluorine atom, and $X^3$ is a phenyl group optionally substituted with at least one group selected from the group consisting of a methyl group, a halogen atom, a cyano group and a nitro group;

The amide compound represented by the formula (1), wherein Z is an oxygen atom, $X^1$ is a methoxy group, and $X^3$ is a fluorine atom;

The amide compound represented by the formula (1), wherein Z is an oxygen atom, $X^1$ is a methoxy group, and $X^3$ is a chlorine atom;

The amide compound represented by the formula (1), wherein Z is an oxygen atom, $X^1$ is a methoxy group, and $X^3$ is a bromine atom;

The amide compound represented by the formula (1), wherein Z is an oxygen atom, $X^1$ is a methoxy group, and $X^3$ is an iodine atom;

The amide compound represented by the formula (1), wherein Z is an oxygen atom, $X^1$ is a methoxy group, and $X^3$ is a C1-C4 alkyl group;

The amide compound represented by the formula (1), wherein Z is an oxygen atom, $X^1$ is a methoxy group, and $X^3$ is a C2-C4 alkenyl group;

The amide compound represented by the formula (1), wherein Z is an oxygen atom, $X^1$ is a methoxy group, and $X^3$ is a C2-C4 alkynyl group;

The amide compound represented by the formula (1), wherein Z is an oxygen atom, $X^1$ is a methoxy group, and $X^3$ is a C1-C4 haloalkyl group;

The amide compound represented by the formula (1), wherein Z is an oxygen atom, $X^1$ is a methoxy group, and $X^3$ is a C1-C4 alkoxy group;

The amide compound represented by the formula (1), wherein Z is an oxygen atom, $X^1$ is a methoxy group, and $X^3$ is a C1-C4 alkylthio group;

The amide compound represented by the formula (1), wherein Z is an oxygen atom, $X^1$ is a methoxy group, and $X^3$ is a nitro group;

The amide compound represented by the formula (1), wherein Z is an oxygen atom, $X^1$ is a methoxy group, and $X^3$ is a cyano group;

The amide compound represented by the formula (1), wherein Z is an oxygen atom, $X^1$ is a methoxy group, and $X^3$ is a formyl group;

The amide compound represented by the formula (1), wherein Z is an oxygen atom, $X^1$ is a methoxy group, and $X^3$ is an $NR^6R^7$ group;

The amide compound represented by the formula (1), wherein Z is an oxygen atom, $X^1$ is a methoxy group, and $X^3$ is a $CO_2R^8$ group;

The amide compound represented by the formula (1), wherein Z is an oxygen atom, $X^1$ is a methoxy group, and $X^3$ is a $CONR^9R^{10}$ group;

The amide compound represented by the formula (1), wherein Z is an oxygen atom, $X^1$ is a methoxy group, and $X^3$ is a phenyl group optionally substituted with at least one group selected from the group consisting of a methyl group, a halogen atom, a cyano group and a nitro group;

The amide compound represented by the formula (1), wherein Z is an oxygen atom;

The amide compound represented by the formula (1), wherein $X^1$ is a fluorine atom;

The amide compound represented by the formula (1), wherein $X^1$ is a methoxy group;

The amide compound represented by the formula (1), wherein Z is an oxygen atom, and $X^1$ is a fluorine atom;

The amide compound represented by the formula (1), wherein Z is an oxygen atom, and $X^1$ is a methoxy group;

The amide compound represented by the formula (1), wherein $X^2$ is a hydrogen atom, a halogen atom or a C1-C4 alkyl group;

The amide compound represented by the formula (1), wherein $X^2$ is a hydrogen atom;

The amide compound represented by the formula (1), wherein $X^2$ is a halogen atom;

The amide compound represented by the formula (1), wherein $X^2$ is a fluorine atom;

The amide compound represented by the formula (1), wherein $X^2$ is a hydrogen atom or a fluorine atom;

The amide compound represented by the formula (1), wherein $X^2$ is a C1-C4 alkyl group;

The amide compound represented by the formula (1), wherein Z is an oxygen atom, and $X^2$ is a hydrogen atom, a halogen atom or a C1-C4 alkyl group;

The amide compound represented by the formula (1), wherein Z is an oxygen atom, and $X^2$ is a hydrogen atom;

The amide compound represented by the formula (1), wherein Z is an oxygen atom, and $X^2$ is a halogen atom;

The amide compound represented by the formula (1), wherein Z is an oxygen atom, and $X^2$ is a fluorine atom;

The amide compound represented by the formula (1), wherein Z is an oxygen atom, and $X^2$ is a hydrogen atom or a fluorine atom;

The amide compound represented by the formula (1), wherein Z is an oxygen atom, and $X^2$ is a C1-C4 alkyl group;

The amide compound represented by the formula (1), wherein $X^3$ is a halogen atom;

The amide compound represented by the formula (1), wherein $X^3$ is a fluorine atom;

The amide compound represented by the formula (1), wherein $X^3$ is a chlorine atom;

The amide compound represented by the formula (1), wherein Z is an oxygen atom, and $X^3$ is a halogen atom;

The amide compound represented by the formula (1), wherein Z is an oxygen atom, and $X^3$ is a fluorine atom;

The amide compound represented by the formula (1), wherein Z is an oxygen atom, and $X^3$ is a chlorine atom;

The amide compound represented by the formula (1), wherein A is $A^1$-$CR^{11}R^{12}R^{13}$;

The amide compound represented by the formula (1), wherein A is $A^1$-$CR^{11}R^{12}R^{13}$, $R^{11}$ is a methyl group or an ethyl group, and $R^{12}$ is a methyl group, an ethyl group, a 1-methylethyl group, a 1,1-dimethylethyl group or a 1-methylpropyl group;

an amide compound represented by the formula (1), wherein A is $A^1$-$CR^{11}R^{12}R^{13}$, and $R^{13}$ is a hydrogen atom or a methyl group;

The amide compound represented by the formula (1), wherein A is $A^1$-$CR^{11}R^{12}R^{13}$, $A^1$ is a single bond, $R^{11}$ is a methyl group, and $R^{12}$ is a 1-methylethyl group or a 1,1-dimethylethyl group, and $R^{13}$ is a hydrogen atom;

The amide compound represented by the formula (1), wherein A is $A^2$-Cy;

The amide compound represented by the formula (1), wherein A is $A^2$-Cy, and $A^2$ is a single bond;

The amide compound represented by the formula (1), wherein A is $A^2$-Cy, and $A^2$ is a $CH_2$ group;

The amide compound represented by the formula (1), wherein A is $A^2$-Cy, and $A^2$ is a $CH(CH_3)$ group;

The amide compound represented by the formula (1), wherein A is $A^2$-Cy, and Cy is a C3-C6 cycloalkyl group optionally substituted with at least one group selected from the group consisting of a C1-C4 alkyl group, a halogen atom, a hydroxyl group and a cyano group;

The amide compound represented by the formula (1), wherein A is $A^2$-Cy, and Cy is a cyclopropyl group optionally substituted with at least one group selected from the group consisting of a C1-C4 alkyl group, a halogen atom, a hydroxyl group and a cyano group;

The amide compound represented by the formula (1), wherein A is $A^2$-Cy, and Cy is a cyclobutyl group optionally substituted with at least one group selected from the group consisting of a C1-C4 alkyl group, a halogen atom, a hydroxyl group and a cyano group;

The amide compound represented by the formula (1), wherein A is $A^2$-Cy, and Cy is a cyclopentyl group optionally substituted with at least one group selected from the group consisting of a C1-C4 alkyl group, a halogen atom, a hydroxyl group and a cyano group;

The amide compound represented by the formula (1), wherein A is $A^2$-Cy, and Cy is a cyclohexyl group optionally substituted with at least one group selected from the group consisting of a C1-C4 alkyl group, a halogen atom, a hydroxyl group and a cyano group;

The amide compound represented by the formula (1), wherein A is —Cy, and Cy is a cyclohexyl group optionally substituted with at least one group selected from the group consisting of a methyl group, a halogen atom and a hydroxyl group;

The amide compound represented by the formula (1), wherein A is $CH_2$-Cy, and Cy is a cyclohexyl group optionally substituted with at least one group selected from the group consisting of a methyl group, a halogen atom and a hydroxyl group;

The amide compound represented by the formula (1), wherein A is $CH(CH_3)$—Cy, and Cy is a cyclohexyl group optionally substituted with at least one group selected from the group consisting of a methyl group, a halogen atom and a hydroxyl group;

The amide compound represented by the formula (1), wherein A is —Cy, and Cy is a cyclopentyl group optionally substituted with at least one group selected from the group consisting of a methyl group, a halogen atom and a hydroxyl group;

The amide compound represented by the formula (1), wherein A is $CH_2$-Cy, and Cy is a cyclopentyl group optionally substituted with at least one group selected from the group consisting of a methyl group, a halogen atom and a hydroxyl group;

The amide compound represented by the formula (1), wherein A is $CH(CH_3)$-Cy, and Cy is a cyclopentyl group optionally substituted with at least one group selected from the group consisting of a methyl group, a halogen atom and a hydroxyl group;

The amide compound represented by the formula (1), wherein A is -Cy, and Cy is a cyclobutyl group optionally substituted with at least one group selected from the group consisting of a methyl group, a halogen atom and a hydroxyl group;

The amide compound represented by the formula (1), wherein A is $CH_2$-Cy, and Cy is a cyclobutyl group optionally substituted with at least one group selected from the group consisting of a methyl group, a halogen atom and a hydroxyl group;

The amide compound represented by the formula (1), wherein A is $CH(CH_3)$-Cy, and Cy is a cyclobutyl group optionally substituted with at least one group selected from the group consisting of a methyl group, a halogen atom and a hydroxyl group;

The amide compound represented by the formula (1), wherein A is $A^2$-Cy, and Cy is a C4-C6 cycloalkyl group optionally substituted with a methyl group;

The amide compound represented by the formula (1), wherein A is $A^2$-Cy, and Cy is a C4-C6 cycloalkyl group optionally substituted with a halogen atom;

The amide compound represented by the formula (1), wherein A is $A^2$-Cy, and Cy is a C4-C6 cycloalkyl group optionally substituted with a fluorine atom;

The amide compound represented by the formula (1), wherein A is $A^2$-Cy, and Cy is a C4-C6 cycloalkyl group optionally substituted with a chlorine atom;

The amide compound represented by the formula (1), wherein A is $A^2$-Cy, and Cy is a C4-C6 cycloalkyl group optionally substituted with a hydroxyl group;

The amide compound represented by the formula (1), wherein A is $A^2$-Cy, and Cy is a C4-C6 cycloalkyl group optionally substituted with a halogen atom;

The amide compound represented by the formula (1), wherein A is a 2-methylcyclopentyl group, a 2-fluorocyclopentyl group, a 2-chlorocyclopentyl group, a 2-hydroxycyclopentyl group, a 2-methylcyclohexyl group, a 2-fluorocyclohexyl group, a 2-chlorocyclohexyl group, a 2-hydroxycyclohexyl group, a cyclobutylmethyl group, a cyclopentylmethyl group, a cyclohexylmethyl group, a (1-hydroxycyclobutyl)methyl group, a (1-hydroxycyclopentyl)methyl group, a (1-hydroxycyclohexyl)methyl group, a 1-cyclobutylethyl group, a 1-cyclopentylethyl group, a 1-cyclohexylethyl group, a 1-(1-hydroxycyclobutyl)ethyl group, a 1-(1-hydroxycyclopentyl)ethyl group or a 1-(1-hydroxycyclohexyl)ethyl group;

The amide compound represented by the formula (1), wherein A is a 2-methylcyclopentyl group, a 2-fluorocyclopentyl group, a 2-chlorocyclopentyl group, a 2-hydroxycyclopentyl group, a 2-methylcyclohexyl group, a 2-fluorocyclohexyl group, a 2-chlorocyclohexyl group or a 2-hydroxycyclohexyl group;

The amide compound represented by the formula (1), wherein A is a cyclobutylmethyl group, a cyclopentylmethyl group, a cyclohexylmethyl group, a (1-hydroxycyclobutyl)methyl group, a (1-hydroxycyclopentyl)methyl group, a (1-hydroxycyclohexyl)methyl group, a 1-cyclobutylethyl group, a 1-cyclopentylethyl group, a 1-cyclohexylethyl group, a 1-(1-hydroxycyclobutyl)ethyl group, a 1-(1-hydroxycyclopentyl)ethyl group or a 1-(1-hydroxycyclohexyl)ethyl group;

The amide compound represented by the formula (1), wherein A is a 2-methylcyclohexyl group;

The amide compound represented by the formula (1), wherein A is a 2-chlorocyclohexyl group;

The amide compound represented by the formula (1), wherein A is a cyclohexylmethyl group;

The amide compound represented by the formula (1), wherein A is a (1-hydroxycyclohexyl)methyl group;

The amide compound represented by the formula (1), wherein A is a 1-(1-hydroxycyclohexyl)ethyl group;

The amide compound represented by the formula (1), wherein A is a cyclobutylmethyl group;

The amide compound represented by the formula (1), wherein A is a (1-hydroxycyclobutyl)methyl group;

The amide compound represented by the formula (1), wherein A is a 1-(1-hydroxycyclobutyl)ethyl group;

The amide compound represented by the formula (1), wherein $X^2$ is a hydrogen atom or a halogen atom, and $X^3$ is a halogen atom;

The amide compound represented by the formula (1), wherein $X^1$ is a fluorine atom, $X^2$ is a hydrogen atom or a halogen atom, and $X^3$ is a halogen atom;

The amide compound represented by the formula (1), wherein $X^2$ is a hydrogen atom or a fluorine atom, and $X^3$ is a fluorine atom or a chlorine atom;

The amide compound represented by the formula (1), wherein $X^2$ is a hydrogen atom or a halogen atom, $X^3$ is a halogen atom, and A is $A^1$-$CR^{11}R^{12}R^{13}$;

The amide compound represented by the formula (1), wherein $X^1$ is a fluorine atom, $X^2$ is a hydrogen atom or a halogen atom, $X^3$ is a halogen atom, and A is $A^1$-$CR^{11}R^{12}R^{13}$;

The amide compound represented by the formula (1), wherein $X^2$ is a hydrogen atom or a fluorine atom, $X^3$ is a fluorine atom or a chlorine atom, and A is $A^1$-$CR^{11}R^{12}R^{13}$;

The amide compound represented by the formula (1), wherein $X^1$ is a fluorine atom, $X^2$ is a hydrogen atom or a fluorine atom, $X^3$ is a fluorine atom, and A is $A^1$-$CR^{11}R^{12}R^{13}$;

The amide compound represented by the formula (1), wherein $X^2$ is a hydrogen atom or a halogen atom, $X^3$ is a halogen atom, A is $A^1$-$CR^{11}R^{12}R^{13}$, and $A^1$ is a single bond;

The amide compound represented by the formula (1), wherein $X^1$ is a fluorine atom, $X^2$ is a hydrogen atom or a halogen atom, $X^3$ is a halogen atom, A is $A^1$-$CR^{11}R^{12}R^{13}$ and $A^1$ is a single bond;

The amide compound represented by the formula (1), wherein $X^2$ is a hydrogen atom or a fluorine atom, $X^3$ is a fluorine atom or a chlorine atom, A is $A^1$-$CR^{11}R^{12}R^{13}$ and $A^1$ is a single bond;

The amide compound represented by the formula (1), wherein $X^1$ is a fluorine atom, $X^2$ is a hydrogen atom or a fluorine atom, $X^3$ is a fluorine atom, A is $A^1$-$CR^{11}R^{12}R^{13}$ and $A^1$ is a single bond;

The amide compound represented by the formula (1), wherein $X^2$ is a hydrogen atom or a halogen atom, and $X^3$ is a halogen atom;

The amide compound represented by the formula (1), wherein $X^1$ is a fluorine atom, $X^2$ is a hydrogen atom or a halogen atom, and $X^3$ is a halogen atom;

The amide compound represented by the formula (1), wherein $X^2$ is a hydrogen atom or a fluorine atom, and $X^3$ is a fluorine atom or a chlorine atom;

The amide compound represented by the formula (1), wherein $X^2$ is a hydrogen atom or a halogen atom, $X^3$ is a halogen atom, and A is $A^2$-Cy;

The amide compound represented by the formula (1), wherein $X^1$ is a fluorine atom, $X^2$ is a hydrogen atom or a halogen atom, $X^3$ is a halogen atom, and A is $A^2$-Cy;

The amide compound represented by the formula (1), wherein $X^2$ is a hydrogen atom or a fluorine atom, $X^3$ is a fluorine atom or a chlorine atom, and A is $A^2$-Cy;

The amide compound represented by the formula (1), wherein $X^2$ is a hydrogen atom or a halogen atom, $X^3$ is a halogen atom, A is $A^2$-Cy, $A^2$ is a single bond, a $CH_2$ group or a $CH(CH_3)$ group;

The amide compound represented by the formula (1), wherein $X^1$ is a fluorine atom, $X^2$ is a hydrogen atom or a halogen atom, $X^3$ is a halogen atom, A is $A^2$-Cy, $A^2$ is a single bond, a $CH_2$ group or a $CH(CH_3)$ group;

The amide compound represented by the formula (1), wherein $X^2$ is a hydrogen atom or a fluorine atom, $X^3$ is a fluorine atom or a chlorine atom, A is $A^2$-Cy, $A^2$ is a single bond, a $CH_2$ group or a $CH(CH_3)$ group;

The amide compound represented by the formula (1), wherein Z is an oxygen atom, and A is a 2-methylcyclohexyl group;

The amide compound represented by the formula (1), wherein Z is an oxygen atom, and A is a 2-chlorocyclohexyl group;

The amide compound represented by the formula (1), wherein Z is an oxygen atom, and A is a cyclohexylmethyl group;

The amide compound represented by the formula (1), wherein Z is an oxygen atom, and A is a (1-hydroxycyclohexyl)methyl group;

The amide compound represented by the formula (1), wherein Z is an oxygen atom, and A is a 1-(1-hydroxycyclohexyl)ethyl group;

The amide compound represented by the formula (1), wherein Z is an oxygen atom, and A is a cyclobutylmethyl group;

The amide compound represented by the formula (1), wherein Z is an oxygen atom, and A is a (1-hydroxycyclobutyl)methyl group; and The amide compound represented by the formula (1), wherein Z is an oxygen atom, and A is a 1-(1-hydroxycyclobutyl)ethyl group.

In the present specification, the structural formula of the compound may, for the sake of convenience, represent a certain form of an isomer, but the present invention includes all kinds of active isomers arising from the structure of the compound, such as a geometric isomer, an optical isomer, a stereoisomer and a tautomeric isomer, and a mixture thereof. Thus, it is not limited to the formula described for the sake of convenience, and can be any single isomer or a mixture thereof. Accordingly, the present compound may have an asymmetric carbon atom in the molecule and may potentially contain an optically active isomer and a racemic isomer, but the present invention is not particularly limited thereto, and includes any cases.

The present compound can be produced by, for example, Production Process 1 to Production Process 6 shown hereinafter.

Production Process 1

Among the present compounds, the present compound (5) wherein Z is an oxygen atom can be produced by reacting the compound (2) with the compound (3) in the presence of a dehydration condensing agent.

[Chemical Formula 2]

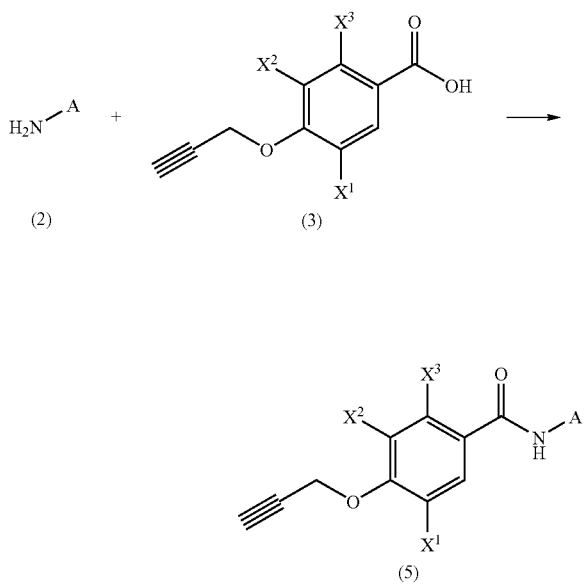

In the formulae, A, $X^1$, $X^2$ and $X^3$ are as defined above.

The reaction is usually carried out in the presence of a solvent.

Examples of the solvent used for the reaction include ethers such as tetrahydrofuran (hereinafter, sometimes, referred to as THF), ethylene glycol dimethyl ether and tert-butyl methyl ether (hereinafter, sometimes, referred to as MTBE); aliphatic hydrocarbons such as hexane and heptane, octane; aromatic hydrocarbons such as toluene and xylene; halogenated hydrocarbons such as chlorobenzene; esters such as butyl acetate and ethyl acetate; nitriles such as acetonitrile; acid amides such as N,N-dimethyl formamide (hereinafter, sometimes, referred to as DMF); sulfoxides such as dimethyl sulfoxide (hereinafter, sometimes, referred to as DMSO); and a mixture thereof.

Examples of the dehydration condensing agent used for the reaction include carbodiimides such as 1-ethyl-3-(3-dimethylaminopropyl)carbodiimide hydrochloride (hereinafter referred to as WSC) and 1,3-dicyclohexylcarbodiimide.

The compound (3) is usually used in the proportion of 1 to 3 mol, and the dehydration condensing agent is usually used in the proportion of 1 to 5 mol per 1 mol of the compound (2).

The reaction temperature is usually within a range of from 0 to 140° C., and the reaction time is usually within a range of from 1 to 24 hours.

After completion of the reaction, the reaction mixture is filtered and the filtrate is extracted with an organic solvent, and then the organic layer is subjected to a post-treatment operation such as drying and concentration, and thus the present compound (5) can be isolated. The isolated present compound (5) can be further purified by chromatography, recrystallization or the like.

Production Process 2

Among the present compounds, the present compound (5) wherein Z is an oxygen atom can be produced by reacting the compound (2) with the compound (4) in the presence of a base.

[Chemical Formula 3]

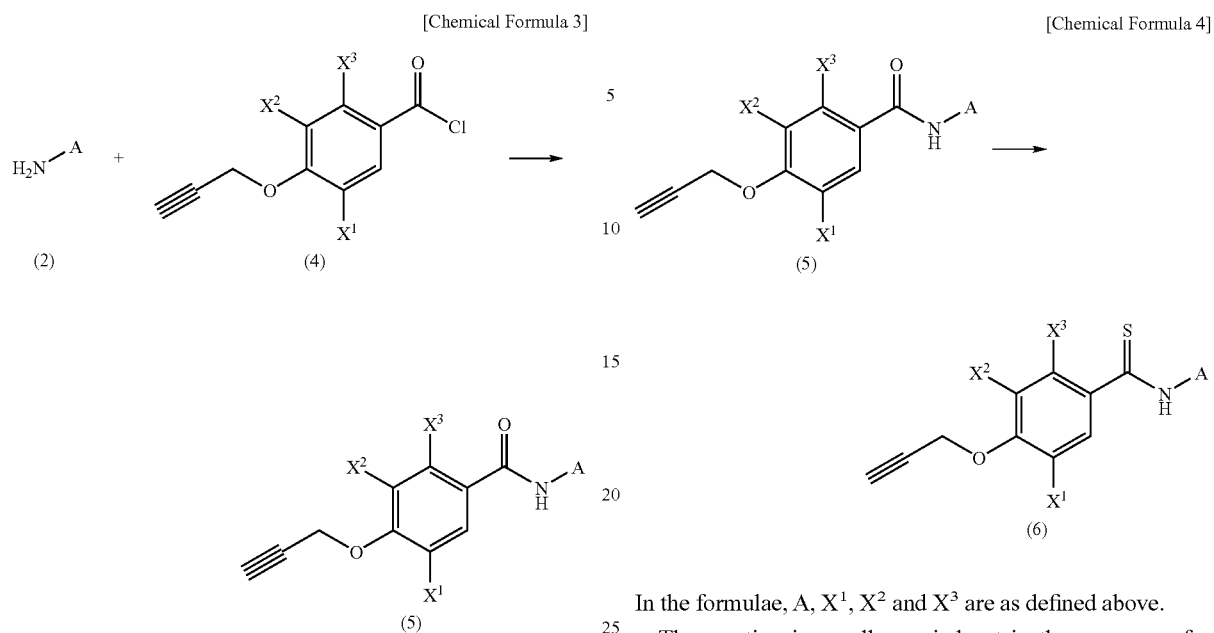

In the formulae, A, X$^1$, X$^2$ and X$^3$ are as defined above.

The reaction is usually carried out in the presence of a solvent.

Examples of the solvent used for the reaction include ethers such as THF, ethylene glycol dimethyl ether and MTBE; aliphatic hydrocarbons such as hexane, heptane and octane; aromatic hydrocarbons such as toluene and xylene; halogenated hydrocarbons such as chlorobenzene; esters such as butyl acetate and ethyl acetate; nitrites such as acetonitrile; acid amides such as DMF; sulfoxides such as DMSO; and a mixture thereof.

Examples of the base used for the reaction include alkali metal carbonates such as sodium carbonate and potassium carbonate; tertiary amines such as triethylamine and diisopropylethylamine; and nitrogen-containing aromatic compounds such as pyridine and 4-dimethylaminopyridine.

The compound (4) is usually used in the proportion of 1 to 3 mol, and the base is usually used in the proportion of 1 to 10 mol per 1 mol of the compound (2).

The reaction temperature is usually within a range of from −20 to 100° C., and the reaction time is usually within a range of from 0.1 to 24 hours.

After completion of the reaction, the reaction mixture is extracted with an organic solvent and the organic layer is subjected to a post-treatment operation such as drying and concentration, and thus the present compound (5) can be isolated. The isolated present compound (5) can be further purified by chromatography, recrystallization or the like.

Production Process 3

Among the present compounds, the present compound (6) wherein Z is a sulfur atom can be produced by reacting, among the present compounds, the present compound (5) wherein Z is an oxygen atom with 2,4-bis(4-methoxyphenyl)-1,3-dithia-2,4-diphosphetane-2,4-disulfide (hereinafter referred to as a Lawesson s reagent).

In the formulae, A, X$^1$, X$^2$ and X$^3$ are as defined above.

The reaction is usually carried out in the presence of a solvent.

Examples of the solvent used for the reaction include ethers such as THF, ethylene glycol dimethyl ether and MTBE; aliphatic hydrocarbons such as hexane, heptane and octane; aromatic hydrocarbons such as toluene and xylene; halogenated hydrocarbons such as chlorobenzene; organic nitrites such as acetonitrile and butyronitrile; sulfoxides such as dimethyl sulfoxide; and a mixture thereof.

The Lawesson's reagent is usually used in the proportion of 1 to 2 mol per 1 mol of the present compound (5).

The reaction temperature is usually within a range of from 25 to 150° C., and the reaction time is usually within a range of from 0.1 to 24 hours.

After completion of the reaction, the reaction mixture is extracted with an organic solvent and the organic layer is subjected to a post-treatment operation such as drying and concentration, and thus the present compound (6) can be isolated. The isolated present compound (6) can be further purified by chromatography, recrystallization or the like.

Production Process 4

Among the present compounds, the present compound (9) wherein Z is an oxygen atom and X$^1$ is a fluorine atom can be produced by reacting the compound (7) with the compound (2) in the presence of a base to obtain the compound (8) (step (IV-1)) and then reacting the compound (8) with propargyl alcohol in the presence of a base (step (IV-2)).

[Chemical Formula 5]

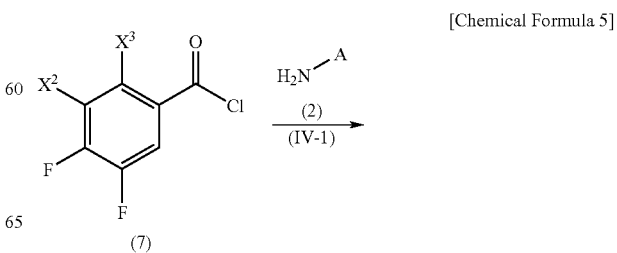

-continued

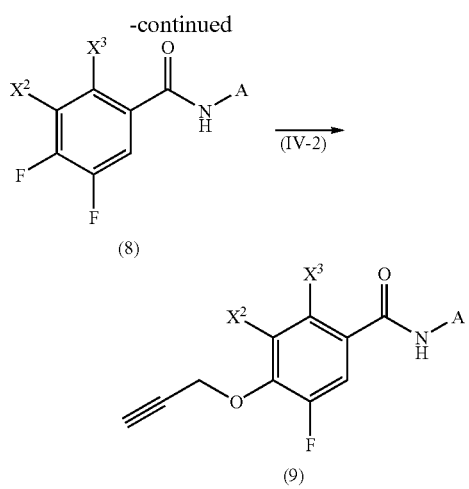

In the formulae, A, $X^2$ and $X^3$ are as defined above.

Step (IV-1)

The reaction is usually carried out in the presence of a solvent.

Examples of the solvent used for the reaction include ethers such as THF, ethylene glycol dimethyl ether and MTBE; aliphatic hydrocarbons such as hexane, heptane and octane; aromatic hydrocarbons such as toluene and xylene; halogenated hydrocarbons such as chlorobenzene; esters such as butyl acetate and ethyl acetate; nitrites such as acetonitrile; acid amides such as DMF; sulfoxides such as dimethyl sulfoxide; and a mixture thereof.

Examples of the base used for the reaction include alkali metal carbonates such as sodium carbonate and potassium carbonate; tertiary amines such as triethylamine and diisopropylethylamine; and nitrogen-containing aromatic compounds such as pyridine and 4-dimethylaminopyridine.

The compound (7) is usually used in the proportion of 1 to 3 mol, and the base is usually used in the proportion of 1 to 10 mol per 1 mol of the compound (2).

The reaction temperature is usually within a range of from −20 to 100° C., and the reaction time is usually within a range of from 0.1 to 24 hours.

After completion of the reaction, the reaction mixture is extracted with an organic solvent and the organic layer is subjected to a post-treatment operation such as drying and concentration, and thus the compound (8) can be isolated. The isolated compound (8) can be further purified by chromatography, recrystallization or the like.

Step (IV-2)

The reaction is usually carried out in the presence of a solvent.

Examples of the solvent used for the reaction include ethers such as THF, ethylene glycol dimethyl ether and MTBE; aliphatic hydrocarbons such as hexane, heptane and octane; ketones such as acetone, methyl ethyl ketone and methyl isobutyl ketone; aromatic hydrocarbons such as toluene and xylene; halogenated hydrocarbons such as chlorobenzene; esters such as butyl acetate and ethyl acetate; nitrites such as acetonitrile; acid amides such as DMF; sulfoxides such as dimethyl sulfoxide; and a mixture thereof.

Examples of the base used for the reaction include alkali metal carbonates such as sodium carbonate and potassium carbonate; alkali metal hydrogen carbonates such as sodium hydrogen carbonate; alkali metal hydrides such as sodium hydride; and alkali metal hydroxides such as sodium hydroxide.

Propargyl alcohol is usually used in the proportion of 1 to 3 mol, and the base is usually used in the proportion of 1 to 2 mol per 1 mol of the compound (8).

The reaction temperature is usually within a range of from −20 to 100° C., and the reaction time is usually within a range of from 0.1 to 24 hours.

After completion of the reaction, the reaction mixture is extracted with an organic solvent and the organic layer is subjected to a post-treatment operation such as drying and concentration, and thus the present compound (9) can be isolated. The isolated present compound (9) can be further purified by chromatography, recrystallization or the like.

Production Process 5

Among the present compounds, the present compound (5) wherein Z is an oxygen atom can be produced by reacting the compound (10) with propargyl bromide in the presence of a base.

[Chemical Formula 6]

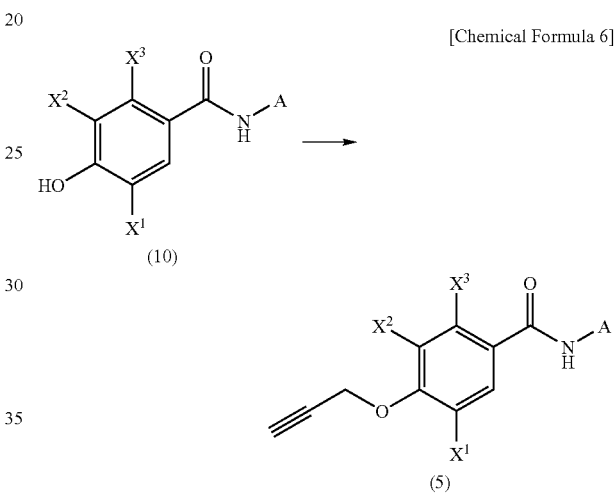

In the formulae, A, $X^1$, $X^2$ and $X^3$ are as defined above.

The reaction is usually carried out in the presence of a solvent.

Examples of the solvent used for the reaction include ethers such as THF, ethylene glycol dimethyl ether and MTBE; aromatic hydrocarbons such as toluene and xylene; halogenated hydrocarbons such as chlorobenzene; nitrites such as acetonitrile; acid amides such as DMF; sulfoxides such as dimethyl sulfoxide; ketones such as acetone, methyl ethyl ketone and methyl isobutyl ketone; water; and a mixture thereof.

Examples of the base used for the reaction include alkali metal carbonates such as sodium carbonate, potassium carbonate and cesium carbonate; alkali metal hydroxides such as sodium hydroxide; and alkali metal hydrides such as sodium hydride.

Propargyl bromide is usually used in the proportion of 1 to 3 mol, and the base is usually used in the proportion of 1 to 3 mol per 1 mol of the compound (10).

The reaction temperature is usually within a range of from −20 to 100° C., and the reaction time is usually within a range of from 0.1 to 24 hours.

After completion of the reaction, the reaction mixture is extracted with an organic solvent and the organic layer is subjected to a post-treatment operation such as drying and concentration, and thus the present compound (5) can be isolated. The isolated present compound (5) can be. further purified by chromatography, recrystallization or the like.

Production Process 6

Among the present compounds, the present compound (12) wherein Z is an oxygen atom, A is $A^2$-Cy, $A^2$ is a single bond, Cy is a 2-fluorocyclohexyl group, a 2-chlorocyclohexyl group, a 2-bromocyclohexyl group, a 2-iodocyclohexyl group or a 2-cyanocyclohexyl group can be produced by the process shown in the following scheme.

Further, the present compound (12) wherein $R^{14}$ is a chlorine atom can be produced without isolating the intermediate (11) by reacting the compound (4) with 7-azabicyclo[4.1.0]heptane.

[Chemical Formula 7]

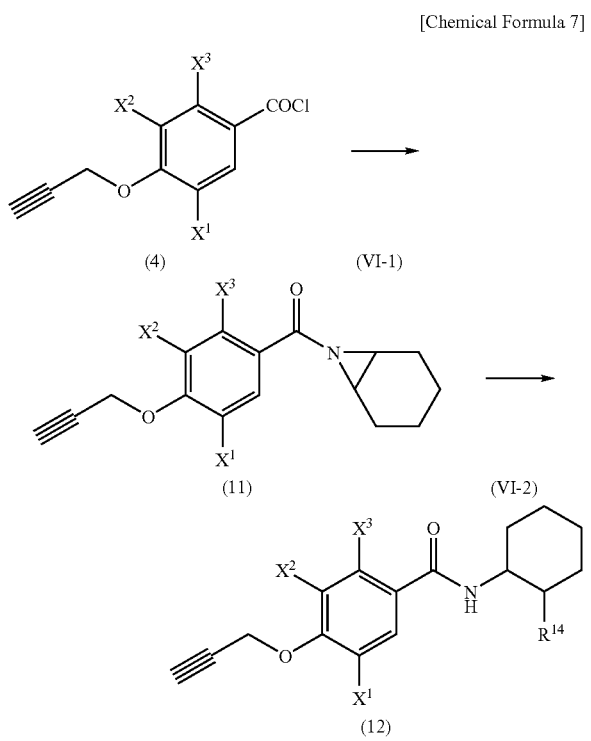

In the formulae, $X^1$, $X^2$ and $X^3$ are as defined above, and $R^{14}$ represents a fluorine atom, a chlorine atom, a bromine atom, an iodine atom or a cyano group.

Step (VI-1)

According to the process described in Production Process 2, the compound (11) can be produced by reacting the compound (4) with 7-azabicyclo[4.1.0]heptane in the presence of a base.

Step (VI-2)

The present compound (12) can be produced by reacting the compound (11) with a reagent described hereinafter.

When $R^{14}$ in the compound (12) is a fluorine atom, examples of the reagent used for the reaction include alkali metal fluorides such as potassium fluoride and lithium fluoride; alkali earth metal fluorides such as calcium fluoride; quaternary ammonium fluorides such as tetrabutylammonium fluoride; and hydrogen fluoride.

When $R^{14}$ in the compound (12) is a chlorine atom, examples of the reagent used for the reaction include alkali metal chlorides such as sodium chloride and lithium chloride; alkali earth metal chlorides such as magnesium chloride; metal chlorides such as aluminum chloride and zinc (II) chloride; quaternary ammonium chlorides such as tetrabutylammonium chloride; organic silicon chlorides such as trimethylsilyl chloride; sulfur compounds such as thionyl chloride; phosphorus compounds such as phosphorus oxychloride, phosphorus trichloride and phosphorus pentachloride; and hydrogen chloride.

When $R^{14}$ in the compound (12) is a bromine atom, examples of the reagent used for the reaction include alkali metal bromides such as sodium bromide; alkali earth metal bromides such as magnesium bromide; metal bromides such as zinc (II) bromide; quaternary ammonium bromides such as tetrabutylammonium bromide; organic silicon bromides such as trimethylsilyl bromide; phosphorus compounds such as phosphorus tribromide; and hydrogen bromide.

When $R^{14}$ in the compound (12) is an iodine atom, examples of the reagent used for the reaction include alkali metal iodides such as potassium iodide; alkali earth metal iodides such as magnesium iodide; metal iodides such as zinc (II) iodide; quaternary ammonium iodides such as tetrabutylammonium iodide; organic silicon compounds such as trimethylsilyl iodide; and hydrogen iodide.

When $R^{14}$ in the compound (12) is a cyano group, examples of the reagent used for the reaction include cyanides such as potassium cyanides and sodium cyanide and the like; and organic silicon compounds such as trimethylsilyl cyanide.

The reaction is usually carried out in the presence of a solvent.

Examples of the solvent used for the reaction include ethers such as THF, ethylene glycol dimethyl ether and MTBE; aromatic hydrocarbons such as toluene and xylene; halogenated hydrocarbons such as chlorobenzene and chloroform; esters such as butyl acetate and ethyl acetate; nitriles such as acetonitrile; acid amides such as DMF; water, and a mixture thereof.

The reagent above is usually used in the proportion of 1 to 10 mol per 1 mol of the compound (11).

The reaction temperature is usually within a range of from −20 to 150° C., and the reaction time is usually within a range of from 0.1 to 24 hours.

After completion of the reaction, the reaction mixture is extracted with an organic solvent and the organic layer is subjected to a post-treatment operation such as drying and concentration, and thus the present compound (12) can be isolated. The isolated present compound (12) can be further purified by chromatography, recrystallization or the like.

Production Process 7

[Chemical Formula 8]

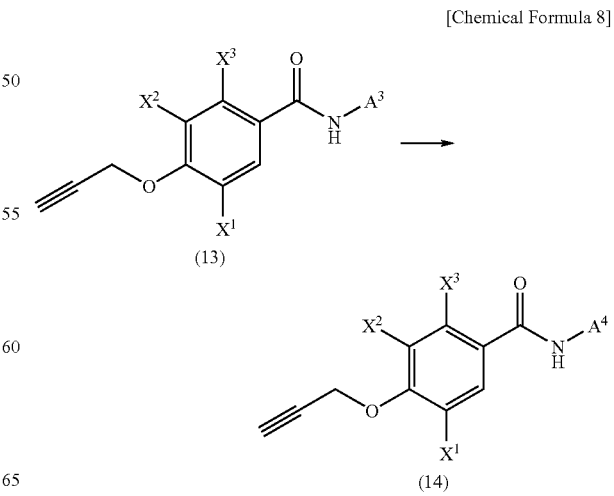

In the formulae, $X^1$, $X^2$ and $X^3$ are as defined above; $A^3$ represents $A^2$-Cy wherein Cy represents a C3-C6 cycloalkyl group substituted with at least one hydroxyl group; and $A^4$ represents $A^2$-Cy and Cy represents a C3-C6 cycloalkyl group substituted with at least one halogen atom.

The present compound (14) can be produced by reacting the compound (13) with a halogenating reagent described hereinafter.

Among the C3-C6 cycloalkyl groups substituted with at least one halogen atom in the present compound (14), when the halogen atom is a fluorine atom, examples of the halogenating reagent used for the reaction include fluorinating agents such as 2,2-difluoro-1,3-dimethylimidazolidine, a hydrogen fluoride pyridine complex, diethyl(1,2,3,3,3-pentafluoro-1-propenyl)amine, di(2-methoxyethyl)sulfur trifluoride, diethylaminosulfur trifluoride, tetrafluorosulfur and N-(2-chloro-1,1,2-trifluoroethyl)diethylamine. Among the C3-C6 cycloalkyl groups substituted with at least one halogen atom in the present compound (14), when the halogen atom is a chlorine atom, examples of the halogenating reagent used for the reaction include chlorinating agents such as thionyl chloride, phosphorus oxychloride, phosphorus trichloride, phosphorus pentachloride and phosgene. Among the C3-C6 cycloalkyl groups substituted with at least one halogen atom in the present compound (14), when the halogen atom is a bromine atom, examples of the halogenating reagent used for the reaction include brominating agents such as phosphorus tribromide.

Examples of the solvent used for the reaction include ethers such as THF, ethylene glycol dimethyl ether and MTBE; aromatic hydrocarbons such as toluene and xylene; halogenated hydrocarbons such as chlorobenzene and chloroform; nitrites such as acetonitrile; and a mixture thereof.

The reagent is usually used in the proportion of 1 to 10 mol per 1 mol of the present compound (13).

The reaction temperature is usually within a range of from −78 to 150° C., and the reaction time is usually within a range of from 0.1 to 24 hours.

After completion of the reaction, the reaction mixture is extracted with an organic solvent and the organic layer is subjected to a post-treatment operation such as drying and concentration, and thus the present compound (14) can be isolated. The isolated present compound (14) can be further purified by chromatography, recrystallization or the like.

A part of intermediates used for the production of the present compound is a commercially available compound or that disclosed in known documents. The intermediate for the production can be produced by, for example, processes disclosed hereinafter.

Intermediate Production Process 1

The compound (3) and the compound (4) can be produced by the process shown in the following scheme.

[Chemical Formula 9]

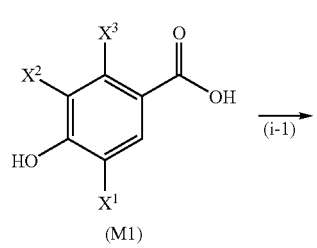

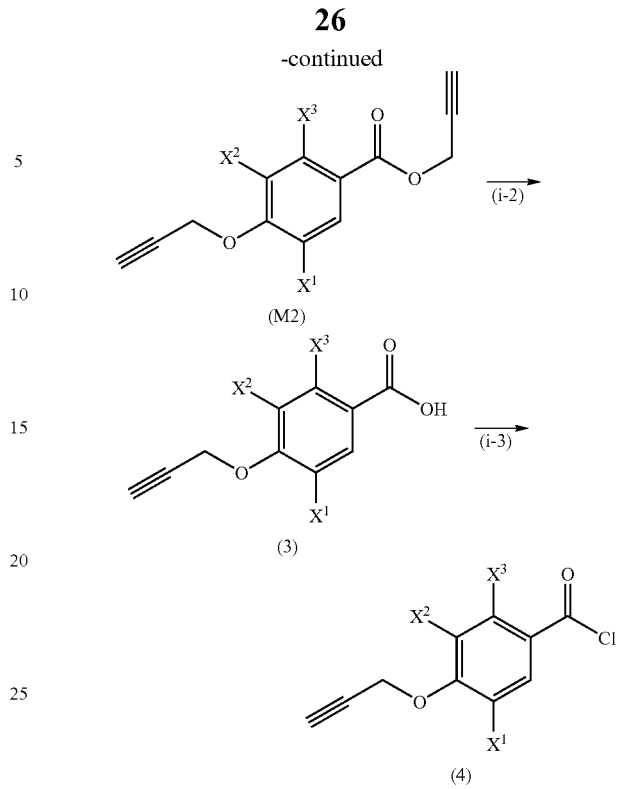

In the formulae, $X^1$, $X^2$ and $X^3$ are as defined above.

Step (i-1)

The compound (M2) can be produced by reacting the compound (M1) with propargyl bromide in the presence of a base.

The reaction is usually carried out in the presence of a solvent.

Examples of the solvent used for the reaction include acid amides such as DMF; and sulfoxides such as DMSO.

Examples of the base used for the reaction include alkali metal carbonates such as sodium carbonate, potassium carbonate and cesium carbonate; and alkali metal hydroxides such as sodium hydroxide.

Propargyl bromide is usually used in the proportion of 2 to 5 mol, and the base is usually used in the proportion of 2 to 5 mol per 1 mol of the compound (M1).

The reaction temperature is usually within a range of from 0 to 140° C., and the reaction time is usually within a range of from 0.5 to 24 hours.

After completion of the reaction, the reaction mixture is extracted with an organic solvent and the organic layer is subjected to a post-treatment operation such as drying and concentration, and thus the compound (M2) can be isolated. The isolated compound (M2) can be further purified by chromatography, recrystallization or the like.

Step (i-2)

The compound (3) can be produced by a hydrolysis reaction of the compound (M2) in the presence of a base.

The reaction is usually carried out in the presence of a solvent.

Examples of the base used for the reaction include alkali metal hydroxides such as sodium hydroxide and potassium hydroxide.

Examples of the solvent used for the reaction include ethers such as tetrahydrofuran, ethylene glycol dimethyl ether and tert-butyl methyl ether; alcohols such as methanol and ethanol; water; and a mixture thereof.

The base is usually used in the proportion of 1 to 10 mol per 1 mol of the compound (M2).

The reaction temperature is usually within a range of from 0 to 120° C., and the reaction time is usually within a range of from 0.5 to 24 hours.

After completion of the reaction, when a solid was precipitated after acidifying the reaction solution, the compound (3) can be isolated by filtration. When a solid is not precipitated, the reaction mixture is extracted with an organic solvent and the organic layer is subjected to a post-treatment operation such as drying and concentration, and thus the compound (3) can be isolated. The isolated compound (3) can be further purified by chromatography, recrystallization or the like.

Step (i-3)

The compound (4) can be produced by reacting the compound (3) with thionyl chloride.

The reaction is usually carried out in the presence of a solvent.

Examples of the solvent used for the reaction include aliphatic hydrocarbons such as hexane, heptane and octane; aromatic hydrocarbons such as toluene and xylene; nitriles such as acetonitrile; halogenated hydrocarbons such as chlorobenzene; acid amides such as DMF; and a mixture thereof.

Thionyl chloride is usually used in the proportion of 1 to 2 mol per 1 mol of the compound (3).

The reaction temperature is usually within a range of from 20 to 120° C., and the reaction time is usually within a range of from 0.1 to 24 hours.

After completion of the reaction, the reaction mixture is subjected to a post-treatment operation such as concentration, and thus the compound (4) can be isolated. The isolated compound (4) can be further purified by chromatography, recrystallization or the like.

Intermediate Production Process 2

The compound (10) can be produced by the process shown in the following scheme.

[Chemical Formula 10]

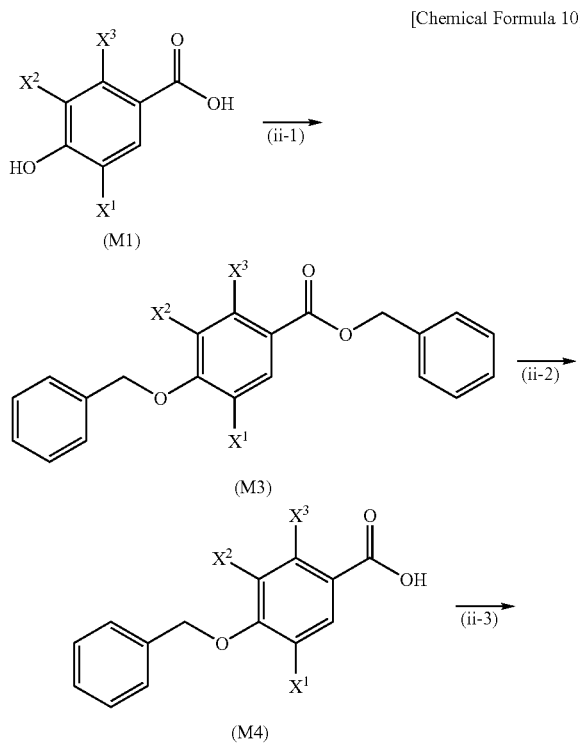

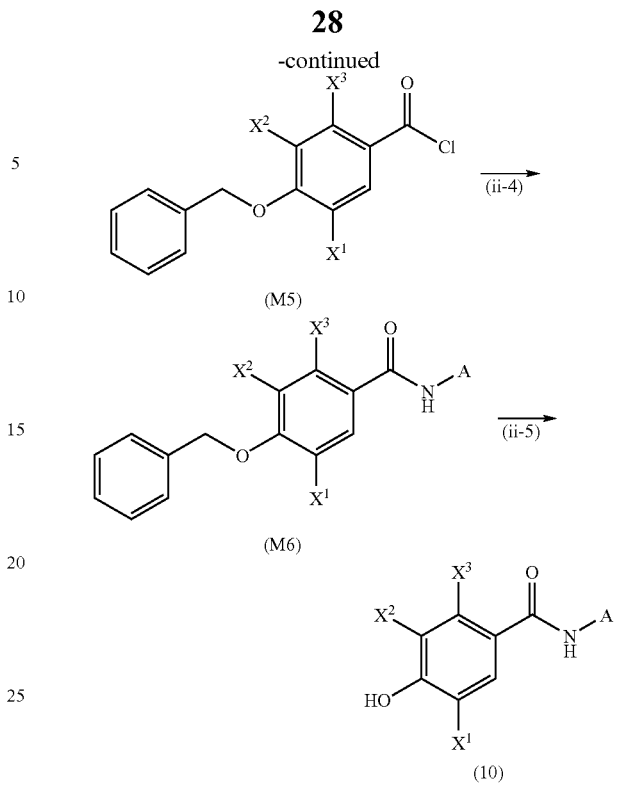

In the formulae, A, $X^1$, $X^2$ and $X^3$ are as defined above.

Step (ii-1)

The compound (M3) can be produced by reacting the compound (M1) with benzyl bromide in the presence of a base.

The reaction is usually carried out in the presence of a solvent.

Examples of the solvent used for the reaction include acid amides such as DMF and sulfoxides such as DMSO.

Examples of the base used for the reaction include alkali metal carbonates such as sodium carbonate, potassium carbonate and cesium carbonate; and alkali metal hydroxides such as sodium hydroxide.

Benzyl bromide is usually used in the proportion of 2 to 5 mol, and the base is usually used in the proportion of 2 to 5 mol per 1 mol of the compound (M1).

The reaction temperature is usually within a range of from 0 to 140° C., and the reaction time is usually within a range of from 0.5 to 24 hours.

After completion of the reaction, the reaction mixture is extracted with an organic solvent and the organic layer is subjected to a post-treatment operation such as drying and concentration, and thus the compound (M3) can be isolated. The isolated compound (M3) can be further purified by chromatography, recrystallization or the like.

Step (ii-2)

The compound (M4) can be produced by a hydrolysis reaction of the compound (M3) in the presence of a base.

The reaction is usually carried out in the presence of a solvent.

Examples of the base used for the reaction include alkali metal hydroxides such as sodium hydroxide and potassium hydroxide.

Examples of the solvent used for the reaction include ethers such as tetrahydrofuran, ethylene glycol dimethyl ether and MTBE; alcohols such as methanol and ethanol; water; and a mixture thereof.

The base is usually used in the proportion of 1 to 10 mol per 1 mol of the compound (M3).

The reaction temperature is usually within a range of from 0 to 120° C., and the reaction time is usually within a range of from 0.5 to 24 hours.

After completion of the reaction, when a solid was precipitated after acidifying the reaction solution, the compound (M4) can be isolated by filtration. When a solid is not precipitated, the reaction mixture is extracted with an organic solvent and the organic layer is subjected to a post-treatment operation such as drying and concentration, and thus the compound (M4) can be isolated. The isolated compound (M4) can be further purified by chromatography, recrystallization or the like.

Step (ii-3)

The compound (M5) can be produced by reacting the compound (M4) with thionyl chloride.

The reaction is usually carried out in the presence of a solvent.

Examples of the solvent used for the reaction include aliphatic hydrocarbons such as hexane, heptane and octane; aromatic hydrocarbons such as toluene and xylene; nitriles such as acetonitrile; halogenated hydrocarbons such as chlorobenzene; acid amides such as DMF; and a mixture thereof.

Thionyl chloride is usually used in the proportion of 1 to 2 mol per 1 mol of the compound (M4).

The reaction temperature is usually within a range of from 20 to 120° C., and the reaction time is usually within a range of from 0.1 to 24 hours.

After completion of the reaction, the reaction mixture is subjected to a post-treatment operation such as concentration, and thus the compound (M5) can be isolated. The isolated compound (M5) can be further purified by chromatography, recrystallization or the like.

Step (ii-4)

According to the process described in Production Process 2, the compound (M6) can be produced by reacting the compound (M5) with the compound (2) in the presence of a base.

Step (ii-5)

The compound (10) can be produced by reacting the compound (M6) with hydrogen in the presence of palladium carbon.

The reaction is usually carried out in the presence of a solvent.

Examples of the solvent used for the reaction include aliphatic hydrocarbons such as hexane, heptane and octane; aromatic hydrocarbons such as toluene and xylene; alcohols such as methanol and ethanol; esters such as ethyl acetate; ethers such as THF and MTBE; water; and a mixture thereof.

Palladium carbon is usually used in the proportion of 0.01 to 0.1 mol, and hydrogen is usually used in the proportion of 1 to 2 mol per 1 mol of the compound (M6).

The reaction temperature is usually within a range of from 0 to 50° C., and the reaction time is usually within a range of from 0.1 to 24 hours. The pressure of hydrogen used for the reaction is within a range of from normal pressure to 10 atmospheric pressure.

After completion of the reaction, the reaction mixture is filtrated and subjected to a post-treatment operation such as concentration, and thus the compound (10) can be isolated. The isolated compound (10) can be further purified by chromatography, recrystallization or the like.

Examples of the compound represented by the formula (3):

[Chemical Formula 11]

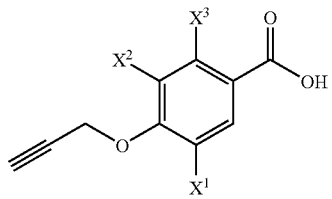

(3)

wherein $X^1$, $X^2$ and $X^3$ are as defined above, which is an intermediate for production of the present compound include the following aspects:

A compound represented by the formula (3), wherein $X^1$ is a fluorine atom;

A compound represented by the formula (3), wherein $X^1$ is a methoxy group;

A compound represented by the formula (3), wherein X is a hydrogen atom;

A compound represented by the formula (3), wherein $X^3$ is a fluorine atom;

A compound represented by the formula (3), wherein $X^1$ and $X^3$ are fluorine atoms;

A compound represented by the formula (3), wherein $X^1$ is a methoxy group, and $X^3$ is a fluorine atom; and A compound represented by the formula (3), wherein $X^2$ is a hydrogen atom, and $X^3$ is a fluorine atom.

Examples of the compound represented by the formula (10):

[Chemical Formula 12]

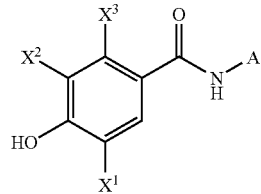

(10)

wherein $X^1$, $X^2$, $X^3$ and A are as defined above, which is an intermediate-for production of the present compound, include the following aspects:

A compound represented by the formula (10), wherein $X^1$ is a fluorine atom;

A compound represented by the formula (10), wherein $X^1$ is a methoxy group;

A compound represented by the formula (10), wherein $X^2$ is a hydrogen atom;

A compound represented by the formula (10), wherein $X^3$ is a fluorine atom;

A compound represented by the formula (10), wherein $X^1$ and $X^3$ are fluorine atoms;

A compound represented by the formula (10), wherein $X^1$ is a methoxy group, and $X^3$ is a fluorine atom; and A compound represented by the formula (10), wherein $X^2$ is a hydrogen atom, and $X^3$ is a fluorine atom.

Examples of the compound represented by the formula (11):

[Chemical Formula 13]

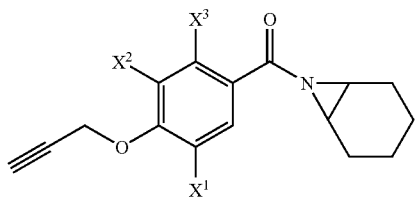

(11)

wherein $X^1$, $X^2$ and $X^3$ are as defined above, which is an intermediate for production of the present compound, include the following aspects:

A compound represented by the formula (11), wherein $X^1$ is a fluorine atom;
A compound represented by the formula (11), wherein $X^1$ is a methoxy group;
A compound represented by the formula (11), wherein $X^2$ is a hydrogen atom;
A compound represented by the formula (11), wherein $X^3$ is a fluorine atom;
A compound represented by the formula (11), wherein $X^1$ and $X^3$ are fluorine atoms; and
A compound represented by the formula (11), wherein $X^1$ is a methoxy group, and $X^3$ is a fluorine atom.

Plant diseases against which the present compound exerts an excellent effect include those caused by fungi, bacteria and viruses. Specific examples of the fungi include genus *Erysiphe* such as wheat powdery mildew (*Erysiphe graminis*), genus *Uncinula* such as grape powdery mildew (*Uncinula necator*), genus *Podosphaera* such as apple powdery mildew (*Podosphaera leucotricha*), genus *Sphaerotheca* such as cucumber powdery mildew (*Sphaerotheca cucurbitae*), genus *Oidiopsis* such as tomato powdery mildew (*Oidiopsis sicula*), genus *Magnaporthe* such as rice blast (*Magnaporthe oryzae*), genus *Cochliobolus* such as rice spot leaf blight (*Cochliobolus miyabeanus*), genus *Mycosphaerella* such as septoria tritici blotch (*Mycosphaerella graminicola*), genus *Pyrenophora* such as barley net blotch (*Pyrenophora teres*), genus *Stagonospora* such as wheat Glume blotch (*Stagonospora nodorum*), genus *Rhynchosporium* such as barley scald disease (*Rhynchosporium secalis*), genus *Pseudocercosporella* such as wheat eyespot (*Pseudocercosporella herpotrichoides*), genus *Gaeumannomyces* such as wheat damping-off (*Gaeumannomyces graminis*), genus *Fusarium* such as wheat scab (*Fusarium* sp.), genus *Microdochium* such as wheat snow mold (*Microdochium nivale*), genus *Venturia* such as apple scab (*Venturia inaequalis*), genus *Elsinoe* such as grape eastern black disease (*Elsinoe ampelina*), genus *Botrytis* such as cucumber gray mold (*Botrytis cinerea*), genus *Monilinia* such as peach brown rot (*Monilinia fructicola*), genus *Phoma* such as rape root rot (*Phoma lingam*), genus *Cladosporium* such as tomato leaf mold (*Cladosporium fulvum*), genus *Cercospora* such as sugarbeet brown spot (*Cercospora beticola*), genus *Cercosporidium* such as peanut late leaf spot (*Cercosporidium personatum*), genus *Colletotrichum* such as strawberry anthracnose (*Colletotrichum fragariae*), genus *Sclerotinia* such as cucumber stem rot (*Sclerotinia sclerotiorum*), genus *Alternaria* such as apple necrotic leaf spot (*Alternaria mali*), genus *Verticillium* such as eggplant *verticillium wilt* (*Verticillium dahliae*), genus *Rhizoctonia* such as rice sheath blight (*Rhizoctonia solani*), genus *Puccinia* such as wheat leaf rust (*Puccinia recondita*), genus *Phakopsora* such as soybean rust (*Phakopsora pachyrhizi*), genus *Tilletia* such as wheat bunt (*Tilletia caries*), genus *Ustilago* such as barley loose smut (*Ustilago nuda*), genus *Sclerotium* such as peanut southern blight (*Sclerotium rolfsii*), genus *Phytophthora* such as potato late blight (*Phytophthora infestans*), genus *Pseudoperonospora* such as. cucumber downy mildew (*Pseudoperonospora cubensis*), genus *Peronospora* such as Chinese cabbage downy mildew (*Peronospora parasitica*), genus *Plasmopara* such as grape downy mildew (*Plasmopara viticola*), genus *Sclerophthora* such as rice downy mildew (*Sclerophthora macrospora*), genus *Pythium* such as cucumber seedling damping-off (*Pythium ultimum*), and genus *Plasmodiophora* such as rapeseed clubroot (*Plasmodiophora brassicae*). Examples of bacteria include genus *Burkholderia* such as bacterial rice seedling blight (*Burkholderia plantarii*), genus *Pseudomonas* such as bacterial cucumber leaf spot (*Pseudomonas syringae* pv. *Lachrymans*), genus *Ralstonia* such as eggplant wilting (*Ralstonia solanacearum*), genus *Xanthomonas* such as Asiatic citrus canker (*Xanthomonas citiri*), and genus *Erwinia* such as Chinese cabbage bacterial soft rot (*Erwinia carotovora*). Examples of viruses include Tobacco mosaic virus and Cucumber mosaic virus. However, the sterilizing spectra should not be limited thereto in any cases.

The plant disease control agent of the present invention can be the present compound itself, but usually, it is used in the form of formulations such as emulsifiable concentrates, wettable powders, granular wettable powders, flowable formulations, dusts and granules produced by mixing it with solid carriers, liquid carriers, surface active agents and other auxiliary agents for formulations. These formulations usually contain the present compound in an amount of 0.1% to 90% by weight.

Examples of the solid carriers used in the formulations include fine powders or particles of minerals such as kaolin clay, attapulgite clay, bentonite, montmorillonite, acid clay, pyrophyllite, talc, diatomaceous earth and calcite; natural organic substances such as corncob powder and walnut shell flour; synthetic organic substances such as urea; salts such as calcium carbonate and ammonium sulfate; and synthetic inorganic substances such as synthetic hydrated silicon hydroxide. Examples of the liquid carriers include aromatic hydrocarbons such as xylene, alkylbenzene and methylnaphthalene; alcohols such as 2-propanol, ethylene glycol, propylene glycol, and cellosolve; ketones such as acetone, cyclohexanone and isophorone; vegetable oils such as soybean oil and cotton seed oil; petroleum aliphatic hydrocarbons; esters; and dimethyl sulfoxide, acetonitrile and water.

Examples of the surfactant include anionic surfactants such as alkyl sulfate, alkyl aryl sulfonate, dialkyl sulfosuccinate, polyoxyethylene alkyl aryl ether phosphate, ligninsulfonate, and naphthalenesulfonate formaldehyde polycondensate; and nonionic surfactants such as polyoxyethylene alkyl aryl ether, polyoxyethylene alkylpolyoxypropylene block copolymer and sorbitan fatty acid ester.

Examples of the auxiliary agent for formulation include water-soluble polymers such as polyvinyl alcohol and polyvinyl pyrrolidone; polysaccharides such as gum Arabic, alginic acid and a salt thereof, CMC (carboxymethyl cellulose), and xanthan gum; inorganic substances such as aluminum magnesium silicate and alumina; preservatives; colorants; PAP (acidic isopropyl phosphate); and stabilizers such as BHT.

The plant disease control agent of the present invention is used for treating plants to protect the plants from plant diseases, and is also used for treating soil to protect plants growing in the soil from plant diseases.

When the plant disease control agent of the present invention is used by subjecting plants to a foliage treatment or used by treating soil, its application amount varies depending upon the kind of crops as plants to be protected, the kind of diseases to be controlled, severity of diseases, form of the formulation, time of application, weather conditions and the like. The total amount of the present compound is usually within a range of from 1 to 5,000 g, and preferably from 5 to 1,000 g per 10,000 $m^2$.

Emulsifiable concentrates, wettable powders and flowable formulations are usually used for treatment by spraying after dilution with water. In this case, the concentration of the present compound is usually within a range from 0.0001 to 3% by weight, and preferably from 0.0005 to 1% by weight. Dusts and granules are usually used for a treatment without being diluted.

The plant disease control agent of the present invention can be used by a treating method such as seed disinfection. Examples of the method include a method of immersing seeds of plants in the plant disease control agent of the present invention in which the concentration of the present compound is adjusted within a range from 1 to 1,000 ppm, a method of spraying or smearing the plant disease control agent of the present invention in which the concentration of the present compound is adjusted within a range from 1 to 1,000 ppm, on seeds of plants, and a method of dust costing of seeds of plants using the plant disease control agent of the present invention.

The plant disease control method of the present invention is usually carried out by treating a plant in which onset of diseases is presumed, or soil where the plant is growing, with an effective amount of the plant disease control agent of the present invention, and/or treating a plant in which onset of diseases has been confirmed, or the soil where the plants are growing.

The plant disease control agent of the present invention is usually used as a plant disease control agent for cultivation, that is, a plant disease control agent for controlling a plant disease in upland fields, paddy fields, orchards, tea fields, pastures, lawn grass fields or the like.

The plant disease control agent of the present invention can also be used in combination with other plant disease control agents, insecticides, acaricides, nematocides, herbicides, plant growth regulators and/or fertilizers.

Examples of the active ingredient of the plant disease control agent include chlorothalonil, fluazinam, dichlofluanid, fosetyl-Al, cyclic imide derivatives (e.g., captan, captafol, folpet, etc.), dithiocarbamate derivatives (e.g., maneb, mancozeb, thiram, ziram, zineb, propineb, etc.), inorganic or organic copper derivatives (e.g., basic copper sulfate, basic copper chloride, copper hydroxide, oxine-copper, etc.), acylalanine derivatives (e.g., metalaxyl, furalaxyl, ofurace, cyprofuram, benalaxyl, oxadixyl, etc.), strobilurin compounds (e.g., kresoxim-methyl, azoxystrobin, trifloxystrobin, picoxystrobin, pyraclostrobin, dimoxystrobin, etc.), anilinopyrimidine derivatives (e.g., cyprodinil, pyrimethanil, mepanipyrim, etc.), phenylpyrrol derivatives (e.g., fenpiclonil, fludioxonil, etc.), imide derivatives (e.g., procymidone, iprodione, vinclozolin, etc.), benzimidazole derivatives (e.g., carbendazim, benomyl, thiabendazole, thiophanate-methyl, etc.), amine derivatives (e.g., fenpropimorph, tridemorph, fenpropidine, spiroxamine, etc.), azole derivatives (e.g., propiconazole, triadimenol, prochloraz, penconazole, tebuconazole, flusilazole, diniconazole, bromuconazole, epoxyconazole, difenoconazole, cyproconazole, metconazole, triflumizole, tetraconazole, myclobutanil, fenbuconazole, hexaconazole, fluquinconazole, triticonazole, bitertanol, imazalil, flutriafol, prothioconazole, etc.), propamocarb, cymoxanil, dimethomorph, famoxadone, fenamidone, pyribencarb, iprovaricarb, benthiavalicarb, mandipropamid, cyazofamid, amisulbrom, zoxamide, ethaboxam, boscalid, fenhexamid, quinoxyfen, proquinazid, metrafenone, cyflufenamide, diethofencarb, fluopicolide, and acibenzolar-S-methyl.

The plant disease control agent of the present invention can be used as a control agent for plant diseases in crop lands such as upland fields, paddy fields, lawn, and orchards, etc. The plant disease control agent can control plant diseases in crop lands where the following "crops" or the like are cultivated.

Field crops: corn, rice, wheat, barley, rye, oat, sorghum, cotton, soybean, peanut, buckwheat, beet, rape, sunflower, sugar cane, tobacco, etc.

Vegetables: Solanaceae (e.g. eggplant, tomato, green pepper, pepper and potato), Cucurbitaceae (e.g. cucumber, pumpkin, zucchini, watermelon and melon), Cruciferae (e.g. Japanese radish, turnip, horseradish, kohlrabi, Chinese cabbage, cabbage, leaf mustard, broccoli and cauliflower), Compositae (e.g. edible burdock, garland chrysanthemum, globe artichoke and lettuce), Liliacede (e.g. Welsh onion, onion, garlic and asparagus), Umbelliferae (e.g. carrot, parsley, celery and Pstinaca), Chenopodiales (e.g. spinach and chard), Lamiaceae (e.g. perilla, mint and basil), strawberry, sweet potato, Chinese yam, taro, etc.

Flowers and ornament plants.

Ornamental foliage plants.

Fruit trees: pomaceous fruits (e.g. apple, pear, Japanese pear, Chinese quince and quince), stone fruits (e.g. peach, plum, nectarine, Japanese apricot, cherry, apricot and prune), citrus fruits (e.g. Satsuma mandarin, orange, lemon, lime and grapefruit), nut trees (e.g. chestnut, walnut, hazel, almond, pistachio, cashew nut and macadamia nut), berries (e.g. blueberry, cranberry, blackberry and raspberry), grape, Japanese persimmon, olive, loquat, banana, coffee, date palm, coconut palm, etc.

Trees other than fruit trees: tea, mulberry, flowering trees and shrubs, street trees (Japanese ash, birch, flowering dogwood, blue gum, ginkgo, lilac, maple, oak, poplar, Chinese redbud, Formosa sweet gum, plane trees, zelkova, Japanese arborvitae, fir, Japanese hemlock, needle juniper, pine, Japanese spruce and Japanese yew).

The above-mentioned "crops" also include crops having resistance to herbicides such as HPPD inhibitors (e.g. isoxaflutol), ALS inhibitos (e.g. imazethapyr and thifensulfuron-methyl), EPSP synthetase inhibitors, glutamine synthetase inhibitors, bromoxynil, etc. which has been imparted by a classic breeding method or a genetic recombination technology.

Examples of the "crops" having the resistance imparted by the classic breeding method include Clearfield® canola resistant to imidazolinone herbicides (e.g. imazethapyr) and STS soybean resistant to sulfonylurea ALS inhibition type herbicides (e.g. thifensulfuron-methyl). As crops having the resistance imparted by the genetic recombination technology, corn cultivars resistant to glyphosate and glufosinate are exemplified and are already on the market under the trade names of RoundupReady® and LibertyLink®.

The above-mentioned "crops" also include crops which have been enabled by the genetic recombination technology to synthesize a selective toxin known in the case of, for example, *Bacillus*.

Examples of toxins produced in such genetically modified plants include insecticidal proteins derived from *Bacillus cereus* and *Bacillus popilliae*; insecticidal proteins such as δ-endotoxins (e.g. Cry1Ab, Cry1Ac, Cry1F, Cry1Fa2, Cry2Ab, Cry3A, Cry3Bb1 and Cry9C), VIP1, VIP2, VIP3, VIP3A, etc., which are derived from *Bacillus thuringiensis*; toxins derived from nematodes; toxins produced by animals, such as scorpion toxin, spider toxin, bee toxin, insect-specific neurotoxins, etc.; filamentous fungi toxins; plant lectins; agglutinin; protease inhibitors such as trypsin inhibitors, serine protease inhibitors, patatin, cystatin, papain inhibitors, etc.; ribosome-inactivating proteins (RIPs) such as ricin, corn-RIP, abrin, rufin, sapolin, briodin, etc.; steroid metabolic enzymes such as 3-hydroxysteroid oxidase, ecdysteroid-UDP-glucosyltransferase, cholesterol oxidase, etc.; ecdysone inhibitors; HMG-COA reductase; ion channel inhibitors such as sodium channel inhibitors, calcium channel inhibitors, etc.; juvenile hormone esterase; diuretic hormone receptors; stilbene synthetase; bibenzyl synthetase; chitinase; and glucanase.

The toxins produced in such genetically engineered crops also include hybrid toxins, partly deficient toxins and modified toxins of insecticidal proteins-such as δ-endotoxin proteins (e.g. Cry1Ab, Cry1Ac, Cry1F, Cry1Fa2, Cry2Ab, Cry3A, Cry3Bb1 and Cry9C), VIP1, VIP2, VIP3, VIP3A, etc. The hybrid toxins are produced by a novel combination of the different domains of such proteins by adopting a recombination technology. As the partly deficient toxin, Cry1Ab deficient in a part of the amino acid sequence is known. In the modified toxins, one or more amino acids of a natural toxin have been replaced.

Examples of such toxins and genetically modified plants capable of synthesizing such toxins are described in EP-A-0 374 753, WO 93/07278, WO 95/34656, EP-A-0 427 529, EP-A-451 878, WO 03/052073, etc.

The toxins contained in such genetically engineered plants impart resistance to insect pests of Coleoptera, insect pests of Diptera and insect pests of Lepidoptera to the plants.

Genetically engineered plants containing one or more insecticidal insect-resistant genes and capable of producing one or more toxins have already been known, and some of them are on the market. Examples of such genetically modified plants include YieldGard® (a corn cultivar capable of producing Cry1Ab toxin), YieldGard Rootworm® (a corn cultivar capable of producing Cry3Bb1 toxin), YieldGard Plus® (a corn cultivar capable of producing Cry1Ab and Cry3Bb1 toxins), Herculex I® (a corn cultivar capable of producing phosphinotrysin N-acetyltransferase (PAT) for imparting-resistance to Cry1Fa2 toxin and Glyfosinate), NuCOTN33B (a cotton cultivar capable of producing Cry1Ac toxin), Bollgard I® (a cotton cultivar capable of producing Cry1Ac toxin), Bollgard II® (a cotton cultivar capable of producing Cry1Ac and Cry2Ab toxins), VIPCOT® (a cotton cultivar capable of producing VIP toxin), NewLeaf® (a potato cultivar capable of producing Cry3A toxin), NatureGard®, Agrisure® GT Advantage (GA21 glyphosate resistant properties), Agrisure® CB Advantage (Bt11 corn borer (CB) properties), and Protecta®.

The above-mentioned "crops" also include crops having an ability to produce an anti-pathogenic substance having a selective action which has been imparted by a gene recombination technology.

As examples of the anti-pathogenic substance, PR proteins and the like are known (PRPs, EP-A-0 392 225). Such anti-pathogenic substances and genetically engineered plants capable of producing them are described in EP-A-0 392 225, WO 95/33818, EP-A-0 353 191, and the like.

Examples of such anti-pathogenic substances produced by the genetically modified plants include ion channel inhibitors such as sodium channel inhibitors, calcium channel inhibitors (for example, KP1, KP4 and KP6 toxins produced by viruses are known), etc.; stilbene synthase; bibenzyl synthase; chitinase; glucanase; PR proteins; and anti-pathogenic substances produced by microorganisms, such as peptide antibiotics, antibiotics having a heterocyclic ring, protein factors concerned in resistance to plant diseases (which are called plant-disease-resistant genes and are described in WO 03/000906), etc.

It is also possible to use the plant disease control agent of the present invention after mixing with other fungicides, insecticides, acaricides, nematocides, herbicides, plant growth regulators, fertilizers or soil conditioners, or to use the agent without mixing them. Examples of the active ingredients of the plant disease control agent include chlorothalonil, fluazinam, dichlofluanid, fosetyl-Al, cyclic imide derivatives (e.g., captan, captafol, folpet, etc.), dithiocarbamate derivatives (e.g., maneb, mancozeb, thiram, ziram, zineb, propineb, etc.), inorganic or organic copper derivatives (e.g., basic copper sulfate, basic copper chloride, copper hydroxide, oxinecupper, etc.), acylalanine derivatives (e.g., metalaxyl, furalaxyl, ofurace, cyprofuram, benalaxyl, oxadixyl, etc.), strobilurin compounds (e.g., kresoxim-methyl, azoxystrobin, trifloxystrobin, picoxystrobin, pyraclostrobin, fluoxastrobin, metominostrobin, oryzastrobin, enestrobin, dimoxystrobin, etc.), anilinopyrimidine derivatives (e.g., cyprodinil, pyrimethanil, mepanipyrim, etc.), phenylpyrrol derivatives (e.g., fenpiclonil, fludioxonil, etc.), imide derivatives (e.g., procymidone, iprodione, vinclozolin, etc.), benzimidazole derivatives (e.g., carbendazim, benomyl, thiabendazole and thiophanate-methyl, etc.), amine derivatives (e.g., fenpropimorph, tridemorph, fenpropidine, spiroxamine, etc.), azole derivatives (e.g., propiconazole, triadimenol, prochloraz, penconazole, tebuconazole, flusilazole, diniconazole, bromuconazole, epoxyconazole, difenoconazole, cyproconazole, metconazole, triflumizole, tetraconazole, myclobutanil, fenbuconazole, hexaconazole, fluquinconazole, triticonazole, bitertanol, imazalil, flutriafol, ipconazole, pefurazoate, prothioconazole, etc.), triforine, pyrifenox, fenarimol, propamocarb, cymoxanil, dimethomorph, flumorph, famoxadone, fenamidone, pyribencarb, iprovaricarb, benthiavalicarb, mandipropamid, cyazofamid, amisulbrom, zoxamide, ethaboxam, boscalid, penthiopyrad, fluopyram, bixafen, carboxin, oxycarboxin, thifluzamide, flutolanil, mepronil, furametpyr, pencycuron, hymexazol, etridiazole, ferimzone, silthiofam, blasticidin S, kasugamycin, streptomycin, pyrazophos, iprobenfos, edifenphos, isoprothiolane, fthalide, pyroquilon, tricyclazole, carpropamid, diclocymet, fenoxanil, probenazole, tiadinil, isotianil, iminoctadine, guazatine, tolnifanide, tolclofos-methyl, fenhexamid, polyoxin B, quinoxyfen, proquinazid, metrafenone, cyflufenamide, diethofencarb, fluopicolide, and acibenzolar-5-methyl.

EXAMPLES

The present invention will be explained in more detail by way of Production Examples, Formulation Examples and Test Examples, but the present invention is not limited thereto.

First, Production Examples of the present compound are shown.

Production Example 1

To 5 ml of chloroform, 0.30 g of 4-(2-propynyloxy)-2,3,5-trifluorobenzoyl chloride, 0.30 g of triethylamine and 0.30 g of cyclohexylmethylamine were added, followed by stirring at room temperature for 2 hours. The reaction mixture was subjected to silica gel column chromatography, and 0.30 g of N-(cyclohexylmethyl)-4-(2-propynyloxy)-2,3,5-trifluorobenzamide (hereinafter referred to as the present compound 1) was obtained.

Present Compound 1:

[Chemical Formula 14]

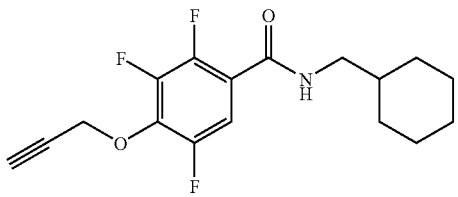

$^1$H-NMR (CDCl$_3$) δ: 0.95-1.31 (5H, m), 1.53-1.79 (6H, m), 2.55 (1H, t, J=2.4 Hz), 3.31-3.34 (2H, m), 4.92 (2H, d, J=2.4 Hz), 6.62 (1H, br s), 7.66 (1H, ddd, J=11.5, 6.6, 2.4 Hz).

Production Example 2

In the same manner as described in Production Example 1, except that 2-methylcyclohexylamine was used in place of cyclohexylmethylamine, N-(2-methylcyclohexyl)-4-(2-propynyloxy)-2,3,5-trifluorobenzamide (hereinafter referred to as the present compound 2) was obtained.

Present Compound 2:

[Chemical Formula 15]

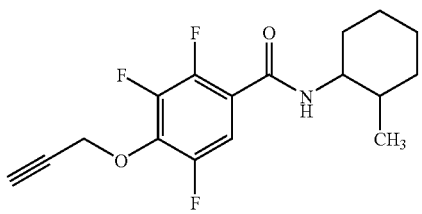

$^1$H-NMR (CDCl$_3$) δ: 0.93 (0.9H, d, J=6.7 Hz), 0.98 (2.1H, d, J=6.7 Hz), 1.09-2.09 (9.0H, m), 2.55-2.57 (1.0H, m), 3.65-3.75 (0.7H, m), 4.26-4.31 (0.3H, m), 4.92-4.93 (2.0H, m), 6.31-6.38 (0.7H, m), 6.63-6.72 (0.3H, m), 7.60-7.68 (1.0H, m)

Production Example 3

In the same manner as described in Production Example 1, except that 1,2-dimethylpropylamine was used in place of cyclohexylmethylamine, N-(1,2-dimethylpropyl)-4-(2-propynyloxy)-2,3,5-trifluorobenzamide (hereinafter referred to as the present compound 3) was obtained.

Present Compound 3:

[Chemical Formula 16]

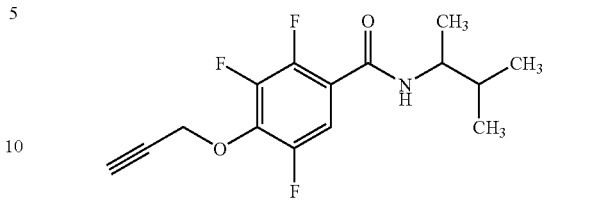

$^1$H-NMR (CDCl$_3$) δ: 0.95 (3H, d, J=3.7 Hz), 0.97 (3H, d, J=3.7 Hz), 1.19 (3H, d, J=6.8 Hz), 1.78-1.86 (1H, m), 2.55 (1H, t, J=2.3 Hz), 4.05-4.15 (1H, m), 4.92 (2H, d, J=2.2 Hz), 6.38-6.44 (1H, m), 7.65 (1H, ddd, J=11.5, 6.6, 2.4 Hz).

Production Example 4

In the same manner as described in Production Example 1, except that trans-2-chlorocyclohexylamine hydrochloride was used in place of cyclohexylmethylamine, trans-N-(2-chlorocyclohexyl)-4-(2-propynyloxy)-2,3,5-trifluorobenzamide (hereinafter referred to as the present compound 4) was obtained.

Present Compound 4:

[Chemical Formula 17]

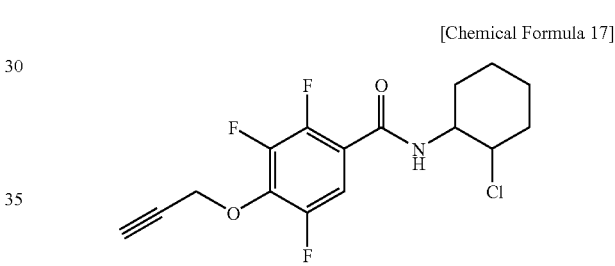

$^1$H-NMR (CDCl$_3$) δ: 1.30-1.53 (3H, m), 1.74-1.85 (3H, m), 2.27-2.34 (2H, m), 2.55 (1H, t, J=2.4 Hz), 3.83-3.89 (1H, m), 4.05-4.14 (1H, m), 4.93 (2H, d, J=2.4 Hz), 6.58-6.63 (1H, m), 7.66 (1H, ddd, J=11.5, 6.6, 2.4 Hz).

Production Example 5

In the same manner as described in Production Example 1, except that (1S)-1-cyclohexylethylamine was used in place of cyclohexylmethylamine, N-((1S)-1-cyclohexylethyl)-4-(2-propynyloxy)-2,3,5-trifluorobenzamide (hereinafter referred to as the present compound 5) was obtained.

Present Compound 5:

[Chemical Formula 18]

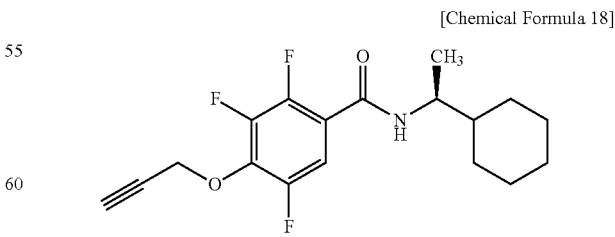

$^1$H-NMR (CDCl$_3$) δ: 0.96-1.30 (8H, m), 1.40-1.48 (1H, m), 1.66-1.82 (5H, m), 2.55 (1H, t, J=2.4 Hz), 4.04-4.13 (1H, m), 4.92 (2H, d, J=2.4 Hz), 6.39-6.44 (1H, m), 7.65 (1H, ddd, J=11.6, 6.7, 2.3 Hz).

Production Example 6

In the same manner as described in Production Example 1, except that 1-cyclobutylethylamine was used in place of cyclohexylmethylamine, N-(1-cyclobutylethyl)-4-(2-propynyloxy)-2,3,5-trifluorobenzamide (hereinafter referred to as the present compound 6) was obtained.

Present Compound 6:

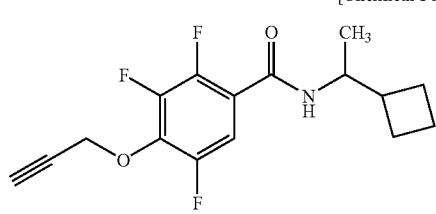

[Chemical Formula 19]

$^1$H-NMR (CDCl$_3$) δ: 1.14 (3H, d, J=6.6 Hz), 1.73-2.07 (6H, m), 2.31-2.41 (1H, m), 2.55 (1H, t, J=2.4 Hz), 4.12-4.21 (1H, m), 4.92 (2H, d, J=2.4 Hz), 6.28-6.32 (1H, m), 7.65 (1H, ddd, J=11.6, 6.7, 2.3 Hz).

Production Example 7

In the same manner as described in Production Example 1, except that 1-(1-hydroxycyclohexyl)methylamine hydrochloride was used in place of cyclohexylmethylamine, N-(1-hydroxycyclohexyl)methyl-4-(2-propynyloxy)-2,3,5-trifluorobenzamide (hereinafter referred to as the present compound 7) was obtained.

Present Compound 7:

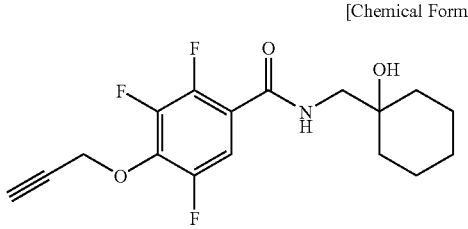

[Chemical Formula 20]

$^1$H-NMR (CDCl$_3$) δ: 1.32-1.63 (10H, m), 1.88 (1H, s); 2.55 (1H, t, J=2.3 Hz), 3.52 (2H, dd, J=5.9, 1.2 Hz), 4.93 (2H, d, J=2.4 Hz), 6.96-7.00 (1H, m), 7.65 (1H, ddd, J=11.6, 6.7, 2.3 Hz)

Production Example 8

In the same manner as described in Production Example 1, except that 4-(2-propynyloxy)-2,5-difluorobenzoyl chloride was used in place of 4-(2-propynyloxy)-2,3,5-trifluorobenzoyl chloride, N-(cyclohexylmethyl)-2,5-difluoro-4-(2-propynyloxy)benzamide (hereinafter referred to as the present compound 8) was obtained.

Present Compound 8:

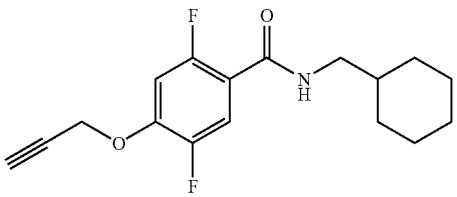

[Chemical Formula 21]

$^1$H-NMR (CDCl$_3$) δ: 0.94-1.31 (5H, m), 1.54-1.79 (6H, m), 2.61 (1H, t, J=2.4 Hz), 3.29-3.33 (2H, m), 4.80 (2H, d, J=2.4 Hz), 6.69-6.74 (1H, m), 6.87 (1H, dd, J=12.7, 6.6 Hz), 7.85 (1H, dd, J=11.7, 7.3 Hz).

Production Example 9

In the same manner as described in Production Example 1, except that 2-methylcyclohexylamine was used in place of cyclohexylmethylamine, and also 4-(2-propynyloxy)-2,5-difluorobenzoyl chloride was used in place of 4-(2-propynyloxy)-2,3,5-trifluorobenzoyl chloride, N-(2-methylcyclohexyl)-2,5-difluoro-4-(2-propynyloxy)benzamide (hereinafter referred to as the present compound 9) was obtained.

Present Compound 9:

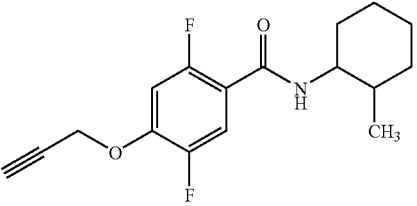

[Chemical Formula 22]

$^1$H-NMR (CDCl$_3$) δ: 0.91-0.99 (3.0H, m), 1.09-2.09 (9.0H, m), 2.60-2.61 (1.0H, m), 3.65-3.75 (0.8H, m), 4.25-4.32 (0.2H, m), 4.79-4.82 (2.0H, m), 6.40 (0.8H, t, J=10.4 Hz), 6.71-6.80 (0.2H, m), 6.82-6.91 (1.0H, m), 7.82-7.88 (1.0H, m).

Production Example 10

In the same manner as described in Production Example 1, except that 1,2-dimethylpropylamine was used in place of cyclohexylmethylamine, and also 4-(2-propynyloxy)-2,5-difluorobenzoyl chloride was used in place of 4-(2-propynyloxy)-2,3,5-trifluorobenzoyl chloride, N-(1,2-dimethylpropyl)-2,5-difluoro-4-(2-propynyloxy)benzamide (hereinafter referred to as the present compound 10) was obtained.

Present Compound 10:

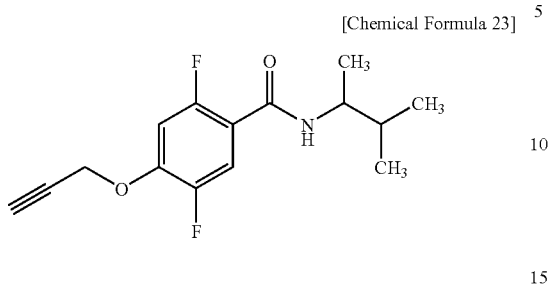

¹H-NMR (CDCl₃) δ: 0.95 (3H, d, J=6.8 Hz), 0.96 (3H, d, J=6.8 Hz), 1.18 (3H, d, J=6.8 Hz), 1.76-1.87 (1H, m), 2.61 (1H, t, J=2.4 Hz), 4.05-4.14 (1H, m), 4.81 (2H, d, J=2.4 Hz), 6.47-6.55 (1H, m), 6.87 (1H, dd, J=12.8, 6.5 Hz), 7.84 (1H, dd, J=11.7, 7.3 Hz).

Production Example 11

In the same manner as described in Production Example 1, except that trans-2-chlorocyclohexylamine hydrochloride was used in place of cyclohexylmethylamine, and also 4-(2-propynyloxy)-2,5-difluorobenzoyl chloride was used in place of 4-(2-propynyloxy)-2,3,5-trifluorobenzoyl chloride, trans-N-(2-chlorocyclohexyl)-2,5-difluoro-4-(2-propynyloxy)benzamide (hereinafter referred to as the present compound 11) was obtained.

Present Compound 11:

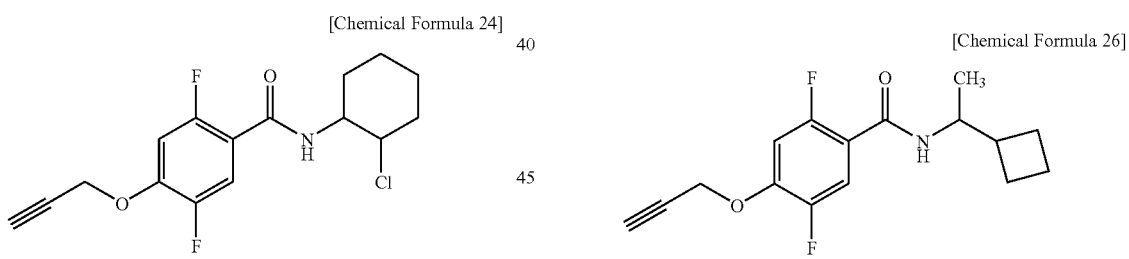

¹H-NMR (CDCl₃) δ: 1.31-1.84 (6H, m), 2.27-2.32 (2H, m), 2.61 (1H, t, J=2.3 Hz), 3.87 (1H, td, J=10.1, 4.1 Hz), 4.07-4.13 (1H, m), 4.81 (2H, d, J=2.2 Hz), 6.68-6.74 (1H, m), 6.88 (1H, dd, J=12.8, 6.5 Hz), 7.86 (1H, dd, J=11.7, 7.3 Hz).

Production Example 12

In the same manner as described in Production Example 1, except that (1S)-1-cyclohexylethylamine was used in place of cyclohexylmethylamine, and also 4-(2-propynyloxy)-2,5-difluorobenzoyl chloride was used in place of 4-(2-propynyloxy)-2,3,5-trifluorobenzoyl chloride, N-((1S)-1-cyclohexylethyl)-2,5-difluoro-4-(2-propynyloxy)benzamide (hereinafter referred to as the present compound 12) was obtained.

Present Compound 12:

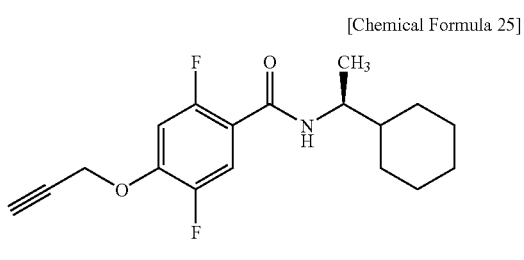

¹H-NMR (CDCl₃) δ: 0.96-1.30 (8H, m), 1.39-1.48 (1H, m), 1.66-1.82 (5H, m), 2.60 (1H, t, J=2.4 Hz), 4.04-4.14 (1H, m), 4.80 (2H, d, J=2.4 Hz), 6.47-6.55 (1H, m), 6.86 (1H, dd, J=12.8, 6.5 Hz), 7.84 (1H, dd, J=11.5, 7.3 Hz).

Production Example 13

In the same manner as described in Production Example 1, except that 1-cyclobutylethylamine was used in place of cyclohexylmethylamine, and also 4-(2-propynyloxy)-2,5-difluorobenzoyl chloride was used in place of 4-(2-propynyloxy)-2,3,5-trifluorobenzoyl chloride, N-(1-cyclobutylethyl)-2,5-difluoro-4-(2-propynyloxy)benzamide (hereinafter referred to as the present compound 13) was obtained.

Present Compound 13:

¹H-NMR (CDCl₃) δ: 1.13 (3H, d, J=6.6 Hz), 1.75-2.07 (6H, m), 2.30-2.41 (1H, m), 2.61 (1H, t, J=2.3 Hz), 4.11-4.22 (1H, m), 4.80 (2H, d, J=2.4 Hz), 6.35-6.43 (1H, m), 6.86 (1H, dd, J=12.8, 6.5 Hz), 7.84 (1H, dd, J=11.7, 7.3 Hz).

Production Example 14

In the same manner as described in Production Example 1, except that 1-(1-hydroxycyclohexyl)methylamine hydrochloride was used in place of cyclohexylmethylamine, and also 4-(2-propynyloxy)-2,5-difluorobenzoyl chloride was used in place of 4-(2-propynyloxy)-2,3,5-trifluorobenzoyl chloride, N-(1-hydroxycyclohexyl)methyl-2,5-difluoro-4-(2-propynyloxy)benzamide (hereinafter referred to as the present compound 14) was obtained.

Present Compound 14:

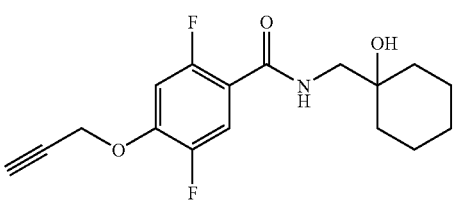
[Chemical Formula 27]

$^1$H-NMR (CDCl$_3$) δ: 1.33-1.64 (10H, m), 2.04 (1H, s), 2.61 (1H, t, J=2.4 Hz), 3.51 (2H, dd, J=5.8, 1.2 Hz); 4.81 (2H, d, J=2.4 Hz), 6.88 (1H, dd, J=12.7, 6.4 Hz), 7.02-7.08 (1H, m), 7.84 (1H, dd, J=11.6, 7.5 Hz).

Production Example 15

In the same manner as described in Production Example 1, except that 2-methylcyclohexylamine was used in place of cyclohexylmethylamine, and also 4-(2-propynyloxy)-2-chloro-5-fluorobenzoyl chloride was used in place of 4-(2-propynyloxy)-2,3,5-trifluorobenzoyl chloride, N-(2-methylcyclohexyl)-2-chloro-5-fluoro-4-(2-propynyloxy) benzamide (hereinafter referred to as the present compound 15) was obtained.

Present Compound 15:

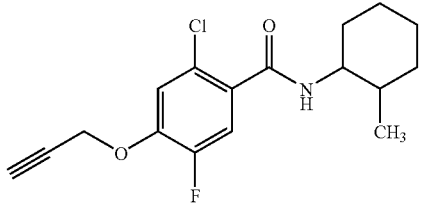
[Chemical Formula 28]

$^1$H-NMR (CDCl$_3$) δ: 0.95 (0.9H, d, J=7.0 Hz), 1.02 (2.1H, d, J=6.5 Hz), 1.09-2.11 (9.0H, m), 2.59-2.62 (1.0H, m), 3.64-3.73 (0.7H, m), 4.25-4.31 (0.3H, m), 4.79-4.81 (2.0H, m), 6.08 (0.7H, d, J=8.7 Hz), 6.52 (0.3H, d, J=8.0 Hz), 7.09-7.13 (1.0H, m), 7.51 (0.7H, d, J=11.3 Hz), 7.62 (0.3H, d, J=11.3 Hz).

Production Example 16

In the same manner as described in Production Example 1, except that 4-(2-propynyloxy)-2-chloro-5-fluorobenzoyl chloride was used in place of 4-(2-propynyloxy)-2,3,5-trifluorobenzoyl chloride, N-(cyclohexylmethyl)-2-chloro-5-fluoro-4-(2-propynyloxy)benzamide (hereinafter referred to as the present compound 16) was obtained.

Present Compound 16:

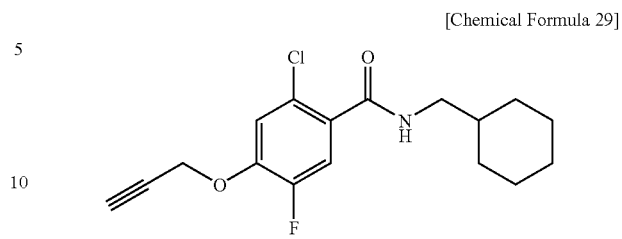
[Chemical Formula 29]

$^1$H-NMR (CDCl$_3$) δ: 0.97-1.31 (5H, m), 1.55-1.81 (6H, m), 2.60 (1H, t, J=2.4 Hz), 3.30 (2H, t, J=6.4 Hz), 4.80 (2H, d, J=2.4 Hz), 6.45 (1H, br s), 7.11 (1H, d, J=7.2 Hz), 7.56 (1H, d, J=11.3 Hz).

Next, Reference Production Examples are shown with respect to an intermediate for the production of the present compound.

Reference Production Example 1

To 50 ml of water, 10 g of 2,3,4,5-tetrafluorobenzoic acid and 4.5 g of sodium hydroxide were added, followed by heating at reflux for 4 hours. The reaction mixture was acidified by adding hydrochloric acid, extracted with ethyl acetate, and then washed in turn with water and saturated brine. The organic layer was dried over magnesium sulfate and concentrated under reduced pressure, and a residue was obtained.

The above-obtained residue, 14 g of propargyl bromide and 18 g of potassium carbonate were added to 100 ml of DMF, followed by stirring at room temperature for 1 day. The reaction mixture was added to water and acidified by adding dilute hydrochloric acid, the acidified mixture was extracted with ethyl acetate. The organic layer was washed in turn with water and saturated brine, dried and then concentrated under reduced pressure. The residue was subjected to silica gel column chromatography, and 6.5 g of 4-(2-propynyloxy)-2,3,5-trifluorobenzoic acid 2-propynyl ester was obtained.

4-(2-Propynyloxy)-2,3,5-trifluorobenzoic acid 2-propynyl ester:

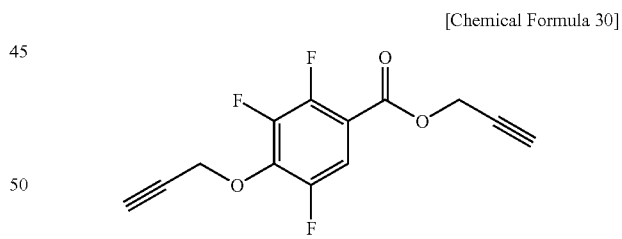
[Chemical Formula 30]

$^1$H-NMR (CDCl$_3$) δ: 2.55 (1H, t, J=2.4 Hz), 2.57 (1H, t, J=2.4 Hz), 4.94 (2H, d, J=2.4 Hz), 4.96 (2H, d, J=2.4 Hz), 7.55 (1H, ddd, J=11.1, 6.1, 2.3 Hz).

To a mixed solution of 10 ml of THF and 10 ml of water, 6.5 g of the obtained 4-(2-propynyloxy)-2,3,5-trifluorobenzoic acid 2-propynyl ester and 2.0 g of lithium hydroxide monohydrate were added, followed by stirring at room temperature for 2 hours and further stirring at 50° C. for 2 hours. The reaction mixture obtained by concentration under reduced pressure until the entire volume was reduced to about half was acidified by adding hydrochloric acid and the obtained solid was collected by filtration. The solid was dried and washed with hexane, and 4.0 g of 4-(2-propynyloxy)-2,3,5-trifluorobenzoic acid was obtained.

4-(2-Propynyloxy)-2,3,5-trifluorobenzoic acid:

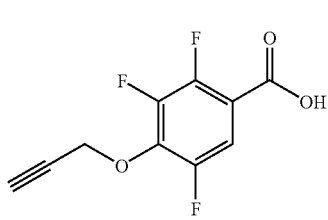

$^1$H-NMR (DMSO-$d_6$) δ: 3.72-3.74 (1H, m), 5.04 (2H, d, J=2.2 Hz), 7.60 (1H, ddd, J=11.2, 6.5, 2.3 Hz)

Reference Production Example 2

To 5 ml of water, 1.0 g of 2,4,5-trifluorobenzoic acid and 0.9 g of sodium hydroxide were added, followed by stirring at 160° C. for 10 minutes using a microwave reactor. The same operation was repeated five times, and the reaction mixtures using 5.0 g in total of 2,4,5-trifluorobenzoic acid were obtained. All the reaction mixtures were combined, acidified by adding hydrochloric acid and then extracted with ethyl acetate. The organic layer was concentrated under reduced pressure to obtain a residue.

To 50 ml of DMF, the residue obtained by the above operation, 9.0 g of propargyl bromide and 10 g of potassium carbonate were added, followed by stirring at room temperature for 2 days. The reaction mixture was extracted with ethyl acetate after adding water. The organic layer was dried over magnesium sulfate and concentrated under reduced pressure, and then the residue was subjected to silica gel column chromatography, and 7.3 g of 2,5-difluoro-4-(2-propynyloxy) benzoic acid 2-propynyl ester was obtained.

2,5-Difluoro-4-(2-propynyloxy)benzoic acid 2-propynyl ester:

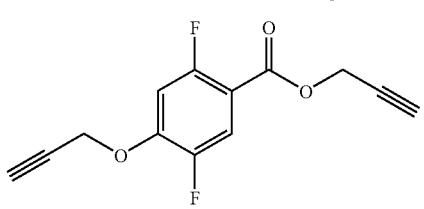

$^1$H-NMR (CDCl$_3$) δ: 2.53 (1H, t, J=2.4 Hz), 2.63 (1H, t, J=2.4 Hz), 4.82 (2H, d, J=2.2 Hz), 4.91 (2H, d, J=2.4 Hz), 6.90 (1H, dd, J=11.6, 6.7 Hz), 7.71 (1H, dd, J=11.1, 6.7 Hz).

To a mixed solution of 20 ml of methanol and 20 ml of an aqueous 15% sodium hydroxide solution, 7.3 g of 2,5-difluoro-4-(2-propynyloxy)benzoic acid 2-propynyl ester was added, followed by stirring at 50° C. for 2 hours. The reaction mixture was added to hydrochloric acid and the obtained solid was collected by filtration. The solid was dried and washed with hexane, and 3.8 g of 2,5-difluoro-4-(2-propynyloxy) benzoic acid was obtained.

2,5-Difluoro-4-(2-propynyloxy)benzoic acid:

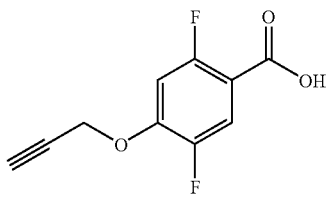

$^1$H-NMR (CDCl$_3$) δ: 2.64 (1H, t, J=2.4 Hz), 4.83 (2H, d, J=2.4 Hz), 6.92 (1H, dd, J=11.5, 6.6 Hz), 7.75 (1H, dd, J=11.1, 6.7 Hz).

To 20 ml of toluene, 1.4 g of 2,5-difluoro-4-(2-propynyloxy)benzoic acid, 0.8 ml of thionyl chloride and 10 mg of DMF were added, and the mixture was heated at reflux for 2 hours. Then, the reaction mixture was concentrated under reduced pressure, and 1.5 g of 2,5-difluoro-4-(2-propynyloxy)benzoyl chloride was obtained.

2,5-Difluoro-4-(2-propynyloxy)benzoyl chloride:

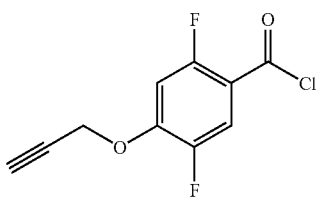

$^1$H-NMR (CDCl$_3$) δ: 2.66 (1H, t, J=2.4 Hz), 4.86 (2H, d, J=2.4 Hz), 6.94 (1H, dd, J=11.7, 6.6 Hz), 7.88 (1H, dd, J=11.1, 6.7 Hz).

Reference Production Example 3

To a mixed solution of 150 ml of DMF, 12.7 g of 2-chloro-4,5-difluorobenzoic acid 2-propynyl ester and 3.4 g of propargyl alcohol, 2.4 g of 60% sodium hydride (oily) was added under ice cooling. After stirring at room temperature overnight, the reaction mixture was added with hydrochloric acid and extracted with ethyl acetate. The obtained organic layer was washed in turn with water and saturated brine, dried over magnesium sulfate and then concentrated under reduced pressure. The obtained residue was subjected to silica gel column chromatography, and 19 g of 2-chloro-5-fluoro-4-(2-propynyloxy)benzoic acid 2-propynyl ester was obtained.

To a mixed solution of 30 ml of methanol and 30 ml of an aqueous 15% sodium hydroxide solution, 19 g of the obtained 2-chloro-5-fluoro-4-(2-propynyloxy)benzoic acid 2-propynyl ester was added, followed by stirring at 50° C. for 2 hours. The reaction mixture was acidified by adding hydrochloric acid and the obtained solid was collected by filtration. The solid was washed with a mixed MTBE-hexane solvent, and 10 g of 2-chloro-5-fluoro-4-(2-propynyloxy)benzoic acid was obtained.

2-Chloro-5-fluoro-4-(2-propynyloxy)benzoic acid:

[Chemical Formula 35]

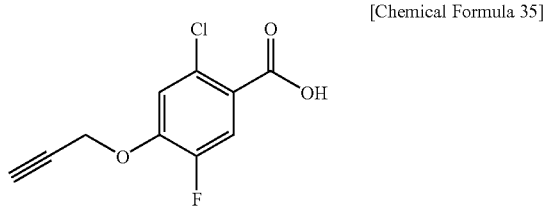

$^1$H-NMR (DMSO-$d_6$) δ: 3.69 (1H, t, J=2.3 Hz), 5.01 (2H, d, J=2.3 Hz), 7.37 (1H, d, J=7.6 Hz), 7.65 (1H, d, J=11.7 Hz).

Next, Formulation Examples are shown. "Parts" are by weight.

Formulation Example 1

A wettable powder of each of the present compounds 1 to 16 is obtained by thoroughly grinding and mixing 50 parts of each of the present compounds, 3 parts of calcium lignosulfonate, 2 parts of magnesium lauryl sulfate and 45 parts of synthetic hydrated silicon oxide.

Formulation Example 2

A flowable formulation of each of the present compounds 1 to 16 is obtained by mixing 20 parts of each of the present compounds and 1.5 parts of sorbitan trioleate with 28.5 parts of an aqueous solution containing 2 parts of a polyvinyl alcohol, finely grinding the resultant mixture by a wet grinding method, adding thereto 40 parts of an aqueous solution containing 0.05 part of xanthan gum and 0.1 part of aluminum magnesium silicate, and then 10 parts of propylene glycol, and stirring and mixing the resulting mixture.

Formulation Example 3

Dust of each of the present compounds 1 to 16 is obtained by thoroughly grinding and mixing 2 parts of each of the present compounds, 88 parts of kaolin clay and 10 parts of talc.

Formulation Example 4

An emulsifiable concentrate of each of the present compounds 1 to 16 is obtained by thoroughly mixing 5 parts of each of the present compounds, 14 parts of polyoxyethylene styryl phenyl ether, 6 parts of calcium dodecylbenzenesulfonate and 75 parts of xylene.

Formulation Example 5

Granules of each of the present compounds 1 to 16 are obtained by thoroughly grinding and mixing 2 parts of each of the present compounds, 1 part of synthetic hydrated silicon oxide, 2 parts of calcium lignosulfonate, 30 parts of bentonite and 65 parts of kaolin clay, thoroughly kneading the resultant mixture with water, and granulating and drying the kneaded product.

Formulation Example 6

A formulation of each of the present compounds 1 to 16 is obtained by mixing 10 parts of each of the present compounds, 35 parts of white carbon containing 50 parts of polyoxyethylene alkyl ether sulfate ammonium salt, and 55 parts of water, and finely grinding the resultant mixture by a wet grinding method.

The following Test Examples show that the present compounds are useful for controlling a plant disease.

The controlling effect was evaluated by visually observing the area or lesion spots on each of test plants at the time of investigation and comparing the area of lesion spots on a plant treated with the present compound with that on an untreated plant.

Test Example 1

Test of preventive effect on rice blast (*Magnaporthe oryzae*))

Each of plastic pots was filled with sandy loam and sown with rice (cultivar: Nihonbare), followed by growing in a greenhouse for 20 days. Each of the present compounds 9 and 10 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the grown rice young seedling. After the foliage application, the plant was air-dried and then grown in contact with a rice seedling (cultivar: Nihonbare) infected with *Magnaporthe oryzae* for 6 days at 24° C. and high humidity in the daytime and at 20° C. and high humidity in the nighttime. Then, the area of lesions was investigated. As a result, it was found that the area of lesion spots on the plant treated with each of the present compounds 9 and 10 was 30% or less of that on an untreated plant.

Test Example 2

Test of Preventive Effect on Wheat Powdery Mildew
(*Erysiphe graminis* f. sp. *tritici*)

Each of plastic pots was filled with sandy loam and sown with wheat (cultivar: Shirogane), followed by growing in a greenhouse for 10 days. The present compound 8 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the grown wheat young seedling. After the foliage application, the plant was air-dried and then inoculated by sprinkling with spores of *Erysiphe graminis* f. sp. *tritici*. After the inoculation, the plant was held in a greenhouse at 23° C. for 7 days and the area of lesion spots was investigated. As a result, it was found that the area of lesion spots on the plant treated with the present compound 8 was 30% or less of that on an untreated plant.

Test Example 3

Test of Curative Effect on Wheat Leaf Rust
(*Puccinia recondita* f. sp. *tritici*)

Each of plastic pots was filled with sandy loam and sown with wheat (cultivar: Shirogane), followed by growing in a greenhouse for 9 days. The plant was inoculated by sprinkling with spores of *Puccinia recondita* f. sp. *tritici*. After the inoculation, the plant was held under darkness and high humidity conditions at 23° C. for 1 day and then air-dried to give a seedling infected with *Puccinia recondita* f. sp. *tritici*. The present compound 10 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the above plant. After the foliage application, the plant was air-dried and held under lighting conditions for 6 days, and then the area of lesions was investigated. As a result, it was found that the area of lesion spots on the plant treated with the present compound 10 was 30% or less of that on an untreated plant.

Test Example 4

Test of Preventive Effect on Wheat Glume Blotch
(*Stagonospora nodorum*)

Each of plastic pots was filled with sandy loam and sown with wheat (cultivar: Shirogane), followed by growing in a greenhouse for 10 days. Each of the present compounds 8 and 9 was formulated into a flowable formulation according to Formulation Example 6. The flowable formulation was diluted to a predetermined concentration (500 ppm) with water, and foliage application of the dilution was carried out. so that the dilution adhered sufficiently to the surfaces of leaves of the grown wheat young seedling. After the foliage application, the plant was air-dried and then inoculated by spraying a water suspension of spores of *Stagonospora nodorum*. After the inoculation, the plant was held under darkness and high humidity conditions at 18° C. for 4 days and held under lighting conditions for 4 days, and then the area of lesion spots was investigated. As a result, it was found that the area of lesion spots on the plant treated with each of the present compounds 8 and 9 was 30% or less of that on an untreated plant.

Test Example 5

Test of Preventive Effect on Wheat *Fusarium* Blight
(*Fusarium culmorum*)

Each of plastic pots was filled with sandy loam and sown with wheat (cultivar: Shirogane), followed by growing in a greenhouse for 10 days. Each of the present compounds 9 and 16 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the grown wheat young seedling. After the foliage application, the plant was air-dried and then inoculated by spraying a water suspension of spores of *Fusarium culmorum*. After the inoculation, the plant was held under darkness and high humidity conditions at 23° C. for 4 days and held under lighting conditions for 3 days, and then the area of lesion spots was investigated. As a result, it was found that the area of lesion spots on the plant treated with each of the present compounds 9 and 16 was 30% or less of that on an untreated plant.

Test Example 6

Test of Preventive Effect on Cucumber Gray Mold
(*Botrytis cinerea*)

Each of plastic pots was filled with sandy loam and sown with cucumber (cultivar: Sagamihanjiro), followed by growing in a greenhouse for 12 days. Each of the present compounds 2, 4, 6, 7, 9, 10, 11, 13 and 14 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the grown cucumber young seedling. After the foliage application, the plant was air-dried and a PDA medium containing spores of *Botrytis cinerea* was placed on the surfaces of the cucumber leaves. After the inoculation, the plant was grown at 12° C. and high humidity for 4 days. Then, the area of lesion spots was investigated. As a result, it was found that the area of lesion spots on the plant treated with each of the present compounds 2, 4, 6, 7, 9, 10, 11, 13 and 14 was 30% or less of that on an untreated plant.

Test Example 7

Test of Preventive Effect on Cucumber Stem Rot
(*Sclerotinia sclerotiorum*)

Each of plastic pots was filled with sandy loam and sown with cucumber (cultivar: Sagamihanjiro), followed by growing in a greenhouse for 12 days. Each of the present compounds 2 to 11, 13 and 14 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the grown cucumber young seedling. After the foliage application, the plant was air-dried and a PDA medium containing mycelia of *Sclerotinia sclerotiorum* was placed on the surfaces of the cucumber leaves. After the inoculation, the plant was grown at 18° C. and high humidity for 4 days. Then, the area of lesion spots was investigated. As a result, it was found that the area of lesion spots on the plant treated with each of the present compounds 2 to 11, 13 and 14 was 30% or less of that on an untreated plant.

Test Example 8

Test of Preventive Effect on Japanese Radish
*Alternaria* Leaf Spot (*Alternaria brassicicola*)

Each of plastic pots was filled with sandy loam and sown with Japanese radish (cultivar: Wase 40-nichi), followed by growing in a greenhouse for 5 days. Each of the present compounds 7, 11, 13 and 14 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the grown Japanese radish young seedling. After the foliage application, the plant was air-dried and then inoculated by spraying a water suspension of spores of *Alternaria brassicicola*. After the inoculation, the plant was held under high humidity conditions at 24° C. for 1 day and held in a greenhouse for 3 days, and then the area of lesion spots was investigated. As a result, it was found that the area of lesion spots on the plant treated with each of the present compounds 7, 11, 13 and 14 was 30% or less of that on an untreated plant.

Test Example 9

Test of Curative Effect on Grape Downy Mildew
(*Plasmopara viticola*)

Each of plastic pots was filled with sandy loam and sown with grape (cultivar: seedling of Berry-A), followed by growing in a greenhouse for 40 days. Each pot was inoculated by spraying a water suspension of zoosporangia of *Plasmopara viticola*, held under high humidity at 23° C. for 1 day and then air-dried to give a seedling infected with *Plasmopara viticola*. Each of the present compounds 6, 10 and 13 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the above grown grape young seedling. After the foliage application, the plant was air-dried and then held in a greenhouse at 23° C. for 5 days and held under high humidity conditions at 23° C. for 1 day, and then the area of lesion spots was investigated. As a result, it was found that the area of lesion spots on the plant treated with each of the present compounds 6, 10 and 13 was 30% or less of that on an untreated plant.

Test Example 10

Test of Preventive Effect on Tomato Late Blight (*Phytophthora infestans*)

Each of plastic pots was filled with sandy loam and sown with tomato (cultivar: Patio), followed by growing in a greenhouse for 20 days. Each of the present compounds 2, 3, 8, 9, 11 and 12 was formulated into a flowable formulation according to Formulation Example 6. The flowable formulation was diluted to a predetermined concentration (500 ppm) with water, and foliage application of the dilution was carried out so that the dilution adhered sufficiently to the surfaces of leaves of the grown tomato young seedling. After the plant was air-dried so that the diluted solution on leaves was dried, a water suspension of zoosporangia of *Phytophthora infestans* was sprayed. After the inoculation, the plant was held under high humidity conditions at 23° C. for 1 day and held in a greenhouse for 4 days, and then the area of lesion spots was investigated. As a result, it was found that the area of lesion spots on the plant treated with each of the present compounds 2, 3, 8, 9, 11 and 12 was 30% or less of that an untreated plant.

INDUSTRIAL APPLICABILITY

According to the present invention, a compound having excellent plant disease control activity can be provided.

The invention claimed is:
1. An amide compound represented by the formula (1):

[Chemical Formula 1]

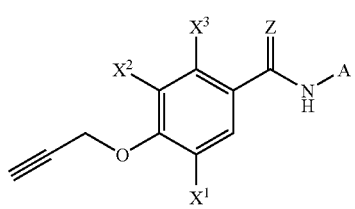

(1)

wherein $X^1$ represents a fluorine atom or a methoxy group;
$X^2$ represents a hydrogen atom, a halogen atom, a C1-C4 alkyl group, a C2-C4 alkenyl group, a C2-C4 alkynyl group, a C1-C4 haloalkyl group, a C1-C4 alkoxy group, a C1-C4 alkylthio group, a hydroxy C1-C4 alkyl group, a nitro group, a cyano group, a formyl group, an $NR^1 R^2$ group, a $CO_2 R^3$ group, a $CONR^4 R^5$ group, or a phenyl group optionally substituted with at least one group selected from the group consisting of a methyl group, a halogen atom, a cyano group and a nitro group;
$X^3$ represents a halogen atom, a C1-C4 alkyl group, a C2-C4 alkenyl group, a C2-C4 alkynyl group, a C1-C4 haloalkyl group, a C1-C4 alkoxy group, a C1-C4 alkylthio group, a nitro group, a cyano group, a formyl group, an $NR^6 R^7$ group, a $CO_2 R^8$ group, a $CONR^9 R^{10}$ group, or a phenyl group optionally substituted with at least one group selected from the group consisting of a methyl group, a halogen atom, a cyano group and a nitro group;
Z represents an oxygen atom or a sulfur atom;
A represents $A^1$-$CR^{11}R^{12}R^{13}$ or $A^2$-Cy;
$A^1$ represents a single bond or a $CH_2$ group;
$A^2$ represents a single bond, a $CH_2$ group, a $CH(CH_3)$ group, a $C(CH_3)_2$ group or a $CH(CH_2 CH_3)$ group;
Cy represents a C3-C6 cycloalkyl group optionally substituted with at least one group selected from the group consisting of a C1-C4 alkyl group, a C2-C4 alkenyl group, a C2-C4 alkynyl group, a halogen atom, a hydroxyl group, a cyano group, a carboxyl group and a C2-C5alkoxycarbonyl group;
$R^1$ and $R^2$ independently represent a hydrogen atom, a C1-C4 alkyl group, a C3-C4alkenyl group, a C3-C4 alkynyl group, a C2-C4 haloalkyl group, a C2-C5 alkylcarbonyl group, a C2-C5 alkoxycarbonyl group or a C1-C4 alkylsulfonyl group;
$R^3$ represents a C1-C4 alkyl group, a C3-C4 alkenyl group or a C3-C4 alkynyl group;
$R^4$ represents a hydrogen atom, a C1-C4 alkyl group, a C3-C4 alkenyl group, a C3-C4 alkynyl group, a C2-C4 haloalkyl group, a C2-C5 alkylcarbonyl group, a C2-C5 alkoxycarbonyl group or a C1-C4 alkylsulfonyl group;
$R^5$ represents a hydrogen atom, a C1-C4 alkyl group, a C3-C4 alkenyl group, a C3-C4 alkynyl group or a C2-C4 haloalkyl group;
$R^6$ and $R^7$ independently represent a hydrogen atom, a C1-C4 alkyl group, a C3-C4 alkenyl group, a C3-C4 alkynyl group, a C2-C4 haloalkyl group, a C2-C5 alkylcarbonyl group, a C2-C5 alkoxycarbonyl group or a C1-C4 alkylsulfonyl group;
$R^8$ represents a C1-C4 alkyl group, a C3-C4 alkenyl group or a C3-C4 alkynyl group;
$R^9$ represents a hydrogen atom, a C1-C4 alkyl group, a C3-C4 alkenyl group, a C3-C4 alkynyl group, a C2-C4 haloalkyl group, a C2-C5 alkylcarbonyl group, a C2-C5 alkoxycarbonyl group or a C1-C4 alkylsulfonyl group;
$R^{10}$ represents a hydrogen atom, a C1-C4 alkyl group, a C3-C4 alkenyl group, a C3-C4 alkynyl group or a C2-C4 haloalkyl group;
$R^{11}$ and $R^{12}$ independently represent a C1-C4 alkyl group; and
$R^{13}$ represents a hydrogen atom, a C1-C4 alkyl group, a C2-C4 alkenyl group, a C2-C4 alkynyl group, a cyano group, a carboxyl group or a C2-C5 alkoxycarbonyl group.

2. The amide compound according to claim 1, wherein $X^3$ is a halogen atom.

3. The amide compound according to claim 1, wherein $X^3$ is a fluorine atom.

4. The amide compound according to claim 1, wherein $X^2$ is a hydrogen atom, a fluorine atom or a methoxy group, and $X^3$ is a fluorine atom.

5. The amide compound according to any one of claims 1 to 4, wherein $X^1$ is a fluorine atom.

6. The amide compound according to any one of claims 1 to 4, wherein $X^1$ is a methoxy group.

7. The amide compound according to claim 1, wherein, in the formula (1), A is $A^1$-$CR^{11}R^{12}R^{13}$, and $R^{13}$ is a hydrogen atom or a methyl group.

8. The amide compound according to claim 1, wherein, in the formula (1), A is $A^2$-Cy, and Cy is a C3-C6 cycloalkyl group optionally substituted with at least one group selected from the group consisting of a C1-C4 alkyl group, a halogen atom, a hydroxyl group and a cyano group.

9. A plant disease control agent comprising the amide compound according to any one of claims 1 to 4 as an active ingredient.

10. A method for controlling a plant disease, which comprises treating a plant or soil with an effective amount of the amide compound according to any one of claims 1 to 4.

11. A plant disease control agent comprising the amide compound according to claim 5 as an active ingredient.

12. A plant disease control agent comprising the amide compound according to claim 6 as an active ingredient.

13. A plant disease control agent comprising the amide compound according to claim 7 as an active ingredient.

14. A plant disease control agent comprising the amide compound according to claim 8 as an active ingredient.

15. A method for controlling a plant disease, which comprises treating a plant or soil with an effective amount of the amide compound according to claim 5.

16. A method for controlling a plant disease, which comprises treating a plant or soil with an effective amount of the amide compound according to claim 6.

17. A method for controlling a plant disease, which comprises treating a plant or soil with an effective amount of the amide compound according to claim 7.

18. A method for controlling a plant disease, which comprises treating a plant or soil with an effective amount of the amide compound according to claim 8.

* * * * *